US012788261B2

(12) United States Patent
McSweeney et al.

(10) Patent No.: US 12,788,261 B2
(45) Date of Patent: Nov. 10, 2026

(54) SYSTEMS AND METHODS FOR CONTINUOUS BLOOD PRESSURE MONITORING

(71) Applicant: Welch Allyn, Inc., Skaneateles Falls, NY (US)

(72) Inventors: Wonkyung McSweeney, Manlius, NY (US); Danielle Endres, Syracuse, NY (US); John A. Lane, Venice, FL (US); David E. Quinn, Auburn, NY (US); Tyson B Whitaker, Arden, NC (US); Gene Wolfe, Pittsford, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

(21) Appl. No.: 18/955,673

(22) Filed: Nov. 21, 2024

(65) Prior Publication Data

US 2025/0160662 A1 May 22, 2025

Related U.S. Application Data

(60) Provisional application No. 63/602,026, filed on Nov. 22, 2023.

(51) Int. Cl.

| | |
|---|---|
| ***A61B 5/021*** | (2006.01) |
| ***A61B 5/00*** | (2006.01) |
| ***A61B 5/11*** | (2006.01) |

(52) U.S. Cl.

CPC ........ *A61B 5/02125* (2013.01); *A61B 5/0044* (2013.01); *A61B 5/1102* (2013.01)

(58) Field of Classification Search

CPC .......................... A61B 5/1102; A61B 5/02125

See application file for complete search history.

(56) References Cited

U.S. PATENT DOCUMENTS

| | | | | |
|---|---|---|---|---|
| 9,980,650 | B2 * | 5/2018 | Bezemer | A61B 5/6898 |
| 10,292,662 | B2 | 5/2019 | Kirenko | |

(Continued)

FOREIGN PATENT DOCUMENTS

| | | | |
|---|---|---|---|
| WO | 2019091517 | A1 | 5/2019 |
| WO | 2023002477 | A1 | 1/2023 |

OTHER PUBLICATIONS

Fred, "Accurate Blood Pressure Measurements and the Other Arm, The Doctor is Ultimately Responsible", Texas Heart Institute Journal, vol. 40, No. 3, 2013, pp. 217-219.

(Continued)

*Primary Examiner* — Angela M Hoffa

(74) *Attorney, Agent, or Firm* — Lee & Hayes, P.C.

(57) ABSTRACT

An imaging system for continuous blood pressure monitoring including determining pulse transit time using ballistocardiography and photoplethysmography is provided. Images received from the imaging system are analyzed to identify heartbeat related micromovements and changes in blood volume at capture points of the body. One or more capture points may have a patch that amplifies heartbeat related movements of the patient's skin beneath the patch. Some patches may include transparent optical filters. Images may be analyzed to identify changes in blood volume at specific capture points on the body using transdermal optical imaging. The micromovements and blood volume may be used to calculate pulse transit time between one or more capture points on the body. Blood pressure may be calculated using the pulse transit time.

8 Claims, 9 Drawing Sheets

(56) References Cited

U.S. PATENT DOCUMENTS

| | | | | |
|---|---|---|---|---|
| 10,398,353 | B2 * | 9/2019 | Addison | A61B 5/1032 |
| 10,660,524 | B2 | 5/2020 | Dubielczyk et al. | |
| 10,849,508 | B2 | 12/2020 | Bhushan et al. | |
| 10,980,430 | B2 | 4/2021 | Przybyszewski et al. | |
| 11,045,095 | B2 | 6/2021 | Tao et al. | |
| 11,147,456 | B2 | 10/2021 | Dubielczyk | |
| 11,272,142 | B2 | 3/2022 | Bresch et al. | |
| 11,589,758 | B2 * | 2/2023 | Pantelopoulos | A61B 5/7264 |
| 12,239,424 | B2 * | 3/2025 | Pantelopoulos | A61B 5/02125 |
| 2014/0221847 | A1 * | 8/2014 | Dubielczyk | A61B 5/0004 600/479 |
| 2014/0243648 | A1 * | 8/2014 | Dubielczyk | A61B 5/14556 600/407 |
| 2014/0253709 | A1 * | 9/2014 | Bresch | H04N 7/18 348/77 |
| 2015/0366455 | A1 * | 12/2015 | Bezemer | A61B 5/6898 600/476 |
| 2016/0278644 | A1 * | 9/2016 | He | A61B 5/7275 |
| 2017/0202463 | A1 * | 7/2017 | Muhlsteff | A61B 5/02125 |
| 2017/0209053 | A1 * | 7/2017 | Pantelopoulos | A61B 5/7278 |
| 2019/0274547 | A1 * | 9/2019 | Ekin | A61B 5/113 |
| 2020/0359917 | A1 | 11/2020 | White et al. | |
| 2021/0393214 | A1 | 12/2021 | Jang et al. | |
| 2023/0293028 | A1 * | 9/2023 | Pantelopoulos | A61B 5/02125 600/301 |

OTHER PUBLICATIONS

Yousefian, P., Shin, S., Mousavi, A et al. "The Potential of Wearable Limb Ballistocardiogram in Blood Pressure Monitoring via Pulse Transit Time." Sci Rep 9, 10666 (2019). https://doi.org/10.1038/s41598-019-46936-9.

* cited by examiner

SYSTEMS AND METHODS FOR CONTINUOUS BLOOD PRESSURE MONITORING

CROSS REFERENCE TO RELATED APPLICATION

This application claims priority to, and benefit of, U.S. Provisional Patent Application No. 63/602,026 filed Nov. 22, 2023, entitled SYSTEMS AND METHODS FOR CONTINUOUS BLOOD PRESSURE MONITORING, the entire contents of which are incorporated herein by reference.

TECHNICAL FIELD

This application relates generally to contactless patient monitoring. Specifically, this application relates to contactless patient monitoring using imaging to capture ballistocardiography (BCG) and photoplethysmography (PPG) readings and the use of those readings to determine blood pressure.

BACKGROUND

Vital signs are objective measurements of essential bodily functions. They generally include body temperature, pulse rate, respiration rate, and blood pressure measurements. However, traditional patient vital sign monitoring is intermittent, providing limited value as it only captures information from a single point in time at a single location on a patient's body. As vital signs may vary depending on where on the body they are taken and may change rapidly in acute situations, traditional vital sign collection is insufficient. For example, the accuracy of a cuff-based blood pressure reading can vary widely due to various factors such as cuff size, cuff placement, limb position, body position, and inflation rate. Further, some individuals find the act of having a cuff placed on their arm to be anxiety-provoking, leading to inaccurate measurements, and putting the patient at risk for adverse events.

Cuff-based blood pressure monitoring relies on a single-point measurement that only provides information about blood pressure at a specific location on the patient at a specific moment in time. It does not provide information about changes over time or during different activities, further, it assumes that the measurement of a single point on the patient's body is reflective of the pressure throughout the body, an assumption that may lead to incorrect diagnoses. For example, postural hypotension and hypertension are difficult to detect using a standard blood pressure cuff, but are valuable measurements, particularly for those at a higher risk of serious cardiovascular events. In patients with occlusions, such as from coronary artery disease, a patient may have different blood pressures at different locations such that the measurement at a single location may provide false information as to the state of the patient as a whole. From a healthcare worker's perspective, the collection of blood pressure measurements is time-consuming and can be burdensome for healthcare workers who are responsible for large numbers of patients. Such information collection may also be disruptive to patients as monitoring may take place around the clock. The use of a traditional blood pressure cuff also requires trained personnel, a problem for patients who need to monitor blood pressure at home or in other settings where there is a shortage of healthcare professionals.

SUMMARY

Traditional patient vital signs monitoring is intermittent and is of limited value in providing an alert for serious unexpected adverse events or rapid changes in the health status of a patient. It also makes assumptions as to the condition of the patient that may be inaccurate. The incidence of adverse patient events is expected to increase due in part to aging populations, increasing complexity of care, pressures to limit care costs, and decreases in available personnel. Continuous monitoring of vital signs may facilitate early detection of adverse events, or identification of deteriorating trends, allowing earlier intervention.

While the early warning score systems generated from traditional monitoring are helpful, there are generally gaps between observations. Further, traditional patient vital sign monitoring at a single location at a single point in time may fail to capture disease states such as possible aneurysm, blockage, stenosis, atherosclerosis, peripheral artery disease, coarctation, dissection, or other intra- and extra-arterial obstruction. Comparisons between blood pressure collected at different points on the body over time may additionally be relevant for individuals with heart disease (atherosclerosis), kidney disease, and diabetes (peripheral artery disease).

Provided are methods and systems for continuous blood pressure monitoring at one or more locations on a patient. Such a system may include a patient monitoring system on one or more servers or other computing devices and may include one or more modules or subroutines, an imaging device, and optionally an illumination device and/or a clinician device. The system described herein may be used to determine blood pressure by capturing information using photoplethysmography (PPG) and ballistocardiography (BCG) and using the PPG and BCG to calculate a patient's pulse transit time (PTT) and from there, blood pressure.

In some aspects, the system may receive images or sets of images of a patient at one or more points in time. The images may then be analyzed to identify visible capture points where measurements may be acquired in both the first set of images and the second set of images. The capture points in each set of images may be the same or different. In some aspects, the capture points may be dynamically selected based on the position of the capture point, the visibility of the capture point, the position of the patient's limbs relative to their heart, and the illumination of the capture point among other criteria. In some aspects, the capture point(s) may include a mechanically deformable and/or retroreflective patch attached to the patient at the capture point(s). The system may then calculate a change in the ratio of oxygenated to deoxygenated blood acquired through an optical filter in the patch or from the patient's skin directly. In some aspects, the system may calculate a change in pixel intensity at one or more capture points between the first set of images and the second set of images and use the change in pixel intensity to calculate PPG or BCG. For example, changes in pixel intensity between image frames may indicate changes in $Hb/HbO_2$ (PPG) and/or changes in the position of the surface of a patient (i.e., a micromovement) (BCG). Such changes in pixel intensity may be, for example, obtained from changes in the mechanically deformable and/or retroreflective patch or from changes in the reflection of the skin. In other aspects, such changes in pixel intensity may be obtained through one or more optical filters in the patch. In some aspects, to calculate the BCG, the system may calculate a change in position at the fiducial point due to a heartbeat at one or more capture points between the first set of images and the second set of images and use the change in position at the fiducial point. The BCG and PPG may then be used to calculate the PTT among other uses. The PTT may then be used to calculate the blood pressure of the patient.

Images may be captured continuously or intermittently using one or more imaging devices such as cameras, video cameras, an infrared camera, an RGB camera, a thermal camera, or other such imaging device to name a few non-limiting examples. In some aspects, the system may include an illumination device to be used in conjunction with the imaging device. The illumination device may be used continuously or intermittently. For example, in some aspects, images may be captured in varying types of illumination including illumination with different wavelengths. In some aspects, the illumination device may be turned off. Images may be captured using the same or different types of illumination. In some aspects, differences in the reflection of the illumination may be taken into consideration when calculating PPG.

The images may be analyzed for variations in pixel intensity. Such variations may be caused by the heartbeat of the patient. In some aspects, the heartbeat may deform or otherwise alter a patch at the capture point, providing information as to BCG and/or PPG. For example, changes in the patch due to changes in blood volume may optically modulate the illumination and therefore the reflection of the illumination captured in the imaging device. Such modulation may be a reflection of a micromovement of the skin of the patient due to changes in blood volume. In some aspects, the patch is retroreflective. In some aspects, the patch may contain its own illumination such as micro-LEDs or fluorescence. In other aspects, the patch may include one or more optical filters such as red filters, green filters, or infrared filters. Such filters may allow, for example, enhancement of the contrast between oxygenated and deoxygenated blood at the capture point. In some aspects, light reflected from the patient through the patch may be captured by the imaging device.

To the accomplishment of the foregoing and related ends, certain illustrative aspects of the system are described herein in connection with the following description and the attached drawings. This summary is provided to introduce a selection of concepts in a simplified form that are further described below in the Detailed Description. This summary is not intended to identify key features or essential features of any subject matter described herein.

DESCRIPTION OF THE FIGURES

The following figures, which form a part of this disclosure, are illustrative of the described technology and are not meant to limit the scope of the claims in any manner.

DETAILED DESCRIPTION

Figure 1:
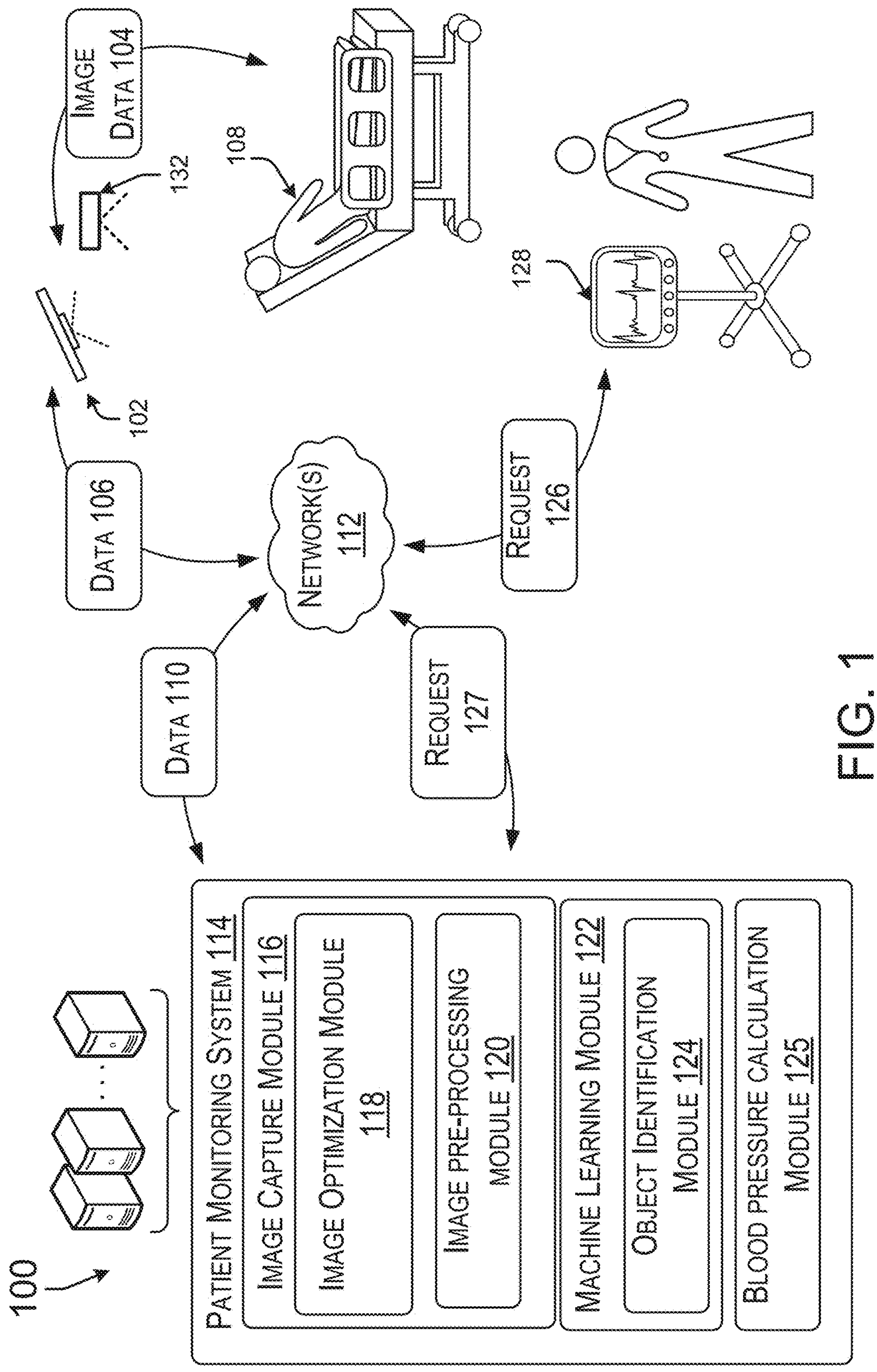
FIG. 1 illustrates a schematic block diagram of an example patient monitoring system environment.

Various implementations of the present disclosure will be described in detail with reference to the drawings, wherein like reference numerals present like parts and assemblies throughout the several views. Additionally, any examples set forth in this specification are not intended to be limiting and merely set forth some of the many possible implementations.

Provided is a system and method for continuous blood pressure monitoring using video or other imaging to capture patient information using ballistocardiography (BCG) and photoplethysmography (PPG). BCG is a non-invasive medical technique that measures the small mechanical movements of the body caused by the heart's contractions. It is a three-dimensional signal indicating the reaction (displacement, velocity, or acceleration) resulting from cardiac ejection of blood and is an integration of multiple forces related to the movements of blood inside the heart and the arteries.

Typically, BCG measurement involves placing sensors on a person's body and recording the vibrations produced by the heart's pumping action. The vibrations are then analyzed to provide information about the heart's function, such as its rate, rhythm, and strength. However, there have been difficulties in the interpretation of BCG as the signal may be dependent on the measurement method, making it challenging to develop a reliable standard (Scarborough WR. Proposals for Ballistocardiographic Nomenclature and Conventions: Revised and Extended: Report of Committee on Ballistocardiographic Terminology. Circulation. 1956; 14:435-450).

PPG is a non-invasive optical technique used to measure the amount of light absorbed by blood, blood vessels, and tissues. These measurements may be used to calculate blood volume changes in the microvasculature bed of tissue such as between the systolic and diastolic phases of the cardiac cycle. The change in volume caused by the pressure pulse of the heart may be detected by measuring the amount of light either transmitted or reflected and identifying landmarks in the captured waveform. Typically, PPG readings are obtained using a wearable device containing a light source and a photodetector. By shining a light with known spectral characteristics optimized to enhance contrast onto the skin and detecting the amount of light that is absorbed or reflected by the underlying blood vessels, wearable PPG may be used to measure heart rate, blood pressure, and oxygen saturation levels. However, current PPG measurement devices have issues with ambient light, accommodating different skin conditions and colors, pressure, and compensating for physical motion artifacts.

As described herein, video and other types of imaging may be used to capture physiological measurements using BCG and PPG and the system may use those measurements to determine pulse transit time (PTT). BCG measurements may be detected by tracking vibrations or other variations in movement (micro-movements) of the skin in response to heartbeats at capture points on the body. PPG measurements may be detected using transdermal optical imaging. By extracting features from the BCG measurements and the PPG measurements, pulse transit time can be calculated. The pulse transit time may then be used to estimate blood pressure (Yousefian P, Shin S, Mousavi A, et al. The potential of wearable limb ballistocardiogram in blood pressure monitoring via pulse transit time. Sci Rep. 2019; 9 (1): 10666).

Pulse transit time refers to the time it takes a pressure wave produced by a left ventricular contraction to travel between two arterial sites within the same cardiac cycle. It is believed to reflect arterial stiffness and may be used to calculate systolic and diastolic blood pressure. While pulse transit time is generally calculated between the aortic valve and a peripheral site, calculations between other locations may provide additional information as to the physiological state of a patient. Pulse transit time has an inversely proportional response to changes in blood pressure. That is, when pulse transit time increases, blood pressure decreases and vice versa.

Figure 6:
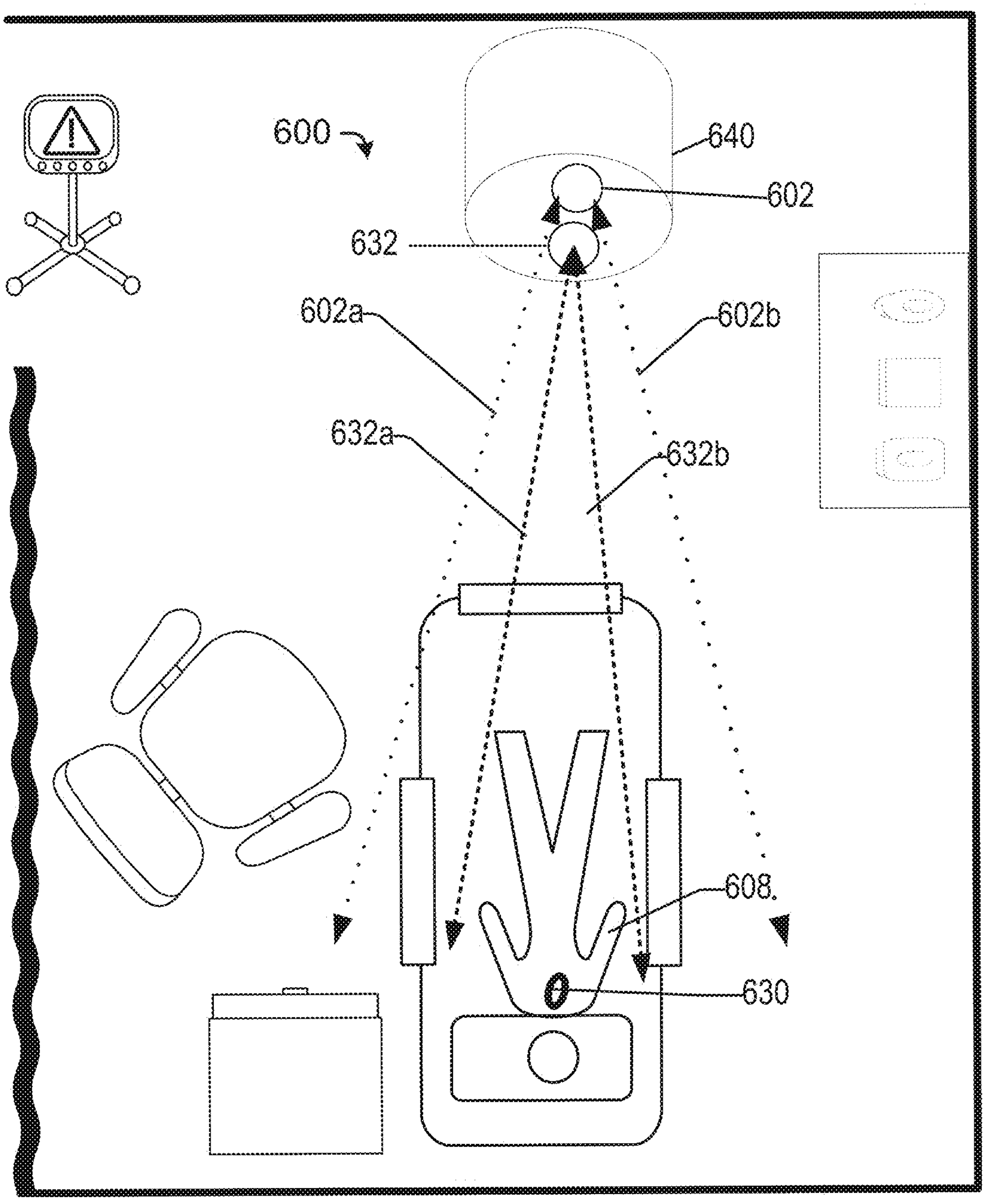
FIG. 6 is a top view of an example patient monitoring system environment according to an embodiment.

FIG. 1 shows a schematic block diagram of an example patient monitoring system environment 100 used to monitor patients. The example patient monitoring system environment 100 includes at least one imaging device 102, a clinician device 128, and a patient monitoring system 114 in communication via one or more networks 112. In some aspects, the patent monitoring system environment 100 may further include an illumination device 132. Such an illumination device may be part of or proximate to the imaging device 102. That is, the imaging device 102 may include an illumination device, alternatively, an illumination device and the imaging device may be separate devices. In some examples, the imaging device 102 and the illumination device 132 may be placed together on a stand or gimbal as shown in FIG. 6, or otherwise positioned such that transmission of structured light from the illumination device may be sent to a patient and the light reflected from the patient may be captured by the imaging device 102. In some aspects, the illumination device 132 may be a ring light in which the imaging device is positioned to collect images through the illumination device. In other aspects, the imaging device and the illumination device may be coaxial. In some aspects, the illumination may be non-diffuse. In some aspects, the patient monitoring system may use the known position of the light source relative to the patient and the angle of the light source to the camera path to calculate the reflection/absorption of the light.

The patient monitoring system 114 may include one or more server computing devices, which may communicate with the imaging device 102 and the clinician device 128 to send and respond to queries, receive data, respond to data, and so forth. Communication between the patient monitoring system 114, the imaging device 102, and/or the clinician device 128 can include imaging data, sensor data, and/or patient data related to the health of the patient. A server of the patient monitoring system 114 may act on requests from the imaging device 102 received via data 106, and/or the clinician device 128 as received by request 126, determine one or more responses to these queries, and respond to the imaging device 102, and/or the clinician device 128 through the network 112. In some aspects, the system may send requests such as request 127 asking for information from the clinician device and/or one or more of the imaging device(s) 102 and illumination device 132. For example, the system may request instructions from the clinician device 128 as to what images to capture, how often to capture the images, or what information to obtain. The system may further request information as to the position(s) of the imaging device 102 and the illumination device 132, request the settings of the imaging device 102, and/or the illumination device 132, and request image data over one or more points in time. A server of the patient monitoring system 114 may also include one or more processors, microprocessors, or other computing devices as discussed in more detail in relation to FIG. 9.

The patient monitoring system 114 may include one or more database systems accessible by a server storing different types of information. For instance, a database can store correlations and algorithms used to manage the imaging data, signal data, and other patient data to be shared between the imaging device 102, the clinician device 128, and/or the patient monitoring system 114. A database can also include clinical data. A database may reside on a server of the patient monitoring system 114 or on a separate computing device(s) accessible by the patient monitoring system 114.

The network 112 is typically any type of wireless network or other communication network known in the art. Examples of network 112 include the Internet, an intranet, a wide area network (WAN), a local area network (LAN), a virtual private network (VPN), cellular network connections, and connections made using protocols such as 802.11a, b, g, n and/or ac. Alternatively or additionally, network 112 may include a nanoscale network, a near-field communication network, a body-area network (BAN), a personal-area network (PAN), a near-me area network (NAN), a campus-area network (CAN), and/or an inter-area network (IAN).

In some examples, the imaging device 102 may include any device having imaging capabilities capable of capturing images of an object in the environment, such as a healthcare setting or a patient's room in a home environment. For example, the imaging device 102 may include a camera, such as a point and shoot camera, a film camera, an SLR camera, a digital camera, an infrared camera, an RGB camera, a thermal camera, or other such imaging device to name a few non-limiting examples. In some examples, the imaging device 102 may include a device capable of capturing still images. Additionally or alternatively, the imaging device 102 may include a video camera that may be capable of capturing a stream of imaging data.

The system disclosed herein allows for the remote determination of PPG and BCG using imaging and structured illumination. For example, measurements may be taken using an imaging system at a known angle to a patient in combination with an illumination source of a specific wavelength offset from or coaxial with the imaging system. The optional illumination device allowing for structured illumination may be part of the imaging device 102 or located elsewhere in the patent monitoring system environment 100 as shown, for example, by the illumination device 132. Such an illumination source may be an LED light such as an RGB LED, a full spectrum light, infrared, 770 nm light, 800 nm light, mid to far infrared (1100+ nm) light, or other light source. In some aspects, a point-source non-diffuse illumination may be used. In some aspects, the illumination device may be used intermittently such that a first set of images is acquired with the illumination and a second set of images is acquired without. In some aspects, images may be taken using different wavelengths of light. For example, a first set of images may be taken using ambient lighting, a second set of images may be taken using a second wavelength, and a third set of images may be taken using a third wavelength in any order. In some aspects, one or more filters may be applied to the structured illumination device or imaging device, for example, a polarizing filter, infrared filter, UV filter, and the like. In some aspects, a complementary filter of the same type or an auxiliary type may be applied to one or the other devices. For example, the filter on the imaging device may be a UV filter and the filter on the illuminator may be infrared. The filter on the illumination device and the filter on the imaging device may be the same or different. In some aspects, one device has a filter, and the other device does not. In some aspects, the illumination may illuminate a patch or other object on the patient that optically modulates the light. That is, the light-reflective surface or the filter changes the structure or characteristic of the light being returned.

The imaging system may be used to collect a high-contrast image of the patient. The image, or series of images, may be used to provide a remote PPG and/or BCG reading for a patient. In some aspects, structured light may be used with the imaging device. For example, structured light may be used to detect changes in perfusion at a capture point. In other aspects, the light may enhance the contrast between $HbO_2$/$dHbO_2$. As the absorption spectra of oxyhemoglobin ($HbO_2$) and deoxyhemoglobin ($dHbO_2$) vary, the use of structured light at different wavelengths may provide a measurement of oxygen saturation based on the ratio between oxygenated and deoxygenated hemoglobin. For example, a first structured light may be at 660 nm and a second structured light may be at 940 nm. Oxygenated hemoglobin absorbs more infrared light at 940 nm and allows more red light to pass through. Deoxygenated hemoglobin allows more infrared light to pass through and absorbs more red light at 660 nm. Subtracting the minimum transmitted light from the peak transmitted light at each wavelength allows for the correction of any effects from other tissues, allowing for remote measurement of exclusively the arterial blood. The ratio of the red light measurement to the infrared light measurement is then calculated and converted to $SpO_2$ based on the Beer-Lambert Law allowing for the capture of PPG measurements. In other aspects, the structured light may be used to capture micromovements on the skin surface of the patient, where the micromovements are due to the heartbeat of the patient, providing BCG readings.

The image capture module 116 may initiate image acquisition via the imaging device 102. Such acquisition may take place automatically in a continuous monitoring environment or may be stopped and/or started via a request, such as a request 126 from the clinician. Captured image data 104 may be sent via network 112 to patient monitoring system 114 as shown via data 106 and data 110. Raw images or pre-processed images may be analyzed to detect the position of the patient as well as mechanical movement and light absorption or reflection from the patient. Pre-processing may be any form of image optimization or calibration performed using one or more devices in or connected to the patient monitoring system environment 100. For example, the patient monitoring system 114 may input the image data into an image optimization module 118 which may alter the image data such that the image data is optimized to be at the highest quality. Such an optimization process may automatically assess the image data and adjust the image data to increase the resolution of the image data, re-format the image data into a correct format, re-size the image data to a correct dimension, or compress the image data, to name few non-limiting examples. In some aspects, the optimization system may crop the image to the area of interest such as a capture point. Thus, by optimizing the image data, the patient monitoring system 114 may obtain more accurate images, thereby more accurately identifying the object(s) in the image data. For example, based on capturing the image data, the imaging device may send the image data to image pre-processing module 120 of the patient monitoring system 114.

The images or sets of images are then analyzed via machine learning. In some examples, the machine learning module 122 may include a machine learning model trained to identify one or more objects in image data. In some aspects, the object identification module 124 may identify the patient, for example through facial recognition or scanning of an object such as a barcode on the wrist of a patient. In some aspects, the imaging device and/or patient monitoring system 114 may identify an object to be tracked throughout a series of images via object identification module 124. For example, an edge of a sheet, or part of an item of clothing may be identified and used as a reference point(s) in the identification of capture points or other patient information. In some aspects, a wearable patch of a specific size, shape, and/or orientation may be used as a reference point as well as for assisting in the acquisition of physiological information using BCG and PPG. In some aspects, the image may be pre-processed using a patient position estimation model to identify a patient orientation and position. In some aspects, range imaging and/or pressure imaging may be used to identify a patient orientation and position. In some aspects, one or more images may be analyzed to determine the relative position of the identified capture point to the heart.

The machine learning model may be trained using training data including other image data including one or more objects and movement of the objects. Using the training data, the machine learning model may be trained to detect and/or identify objects and movement of the objects within the image data. Moreover, the machine learning model may use image data previously input into the machine learning model to continue to train the machine learning model, thus increasing the accuracy of the machine learning model. In some aspects, one or more objects, movements, or reflections identified through the machine learning model may be weighted depending on specifics related to the patient, the patient's condition, or the type of data being collected.

Machine learning may be performed using a wide variety of methods or combinations of methods, such as contrastive learning, supervised learning, unsupervised learning, temporal difference learning, reinforcement learning, and so forth. Some non-limiting examples of supervised learning which may be used with the present technology include AODE (averaged one-dependence estimators), artificial neural network, back propagation, Bayesian statistics, naïve bayes classifier, Bayesian network, Bayesian knowledge base, case-based reasoning, decision trees, inductive logic programming, Gaussian process regression, gene expression programming, group method of data handling (GMDH), learning automata, learning vector quantization, minimum message length (decision trees, decision graphs, etc.), lazy learning, instance-based learning, nearest neighbor algorithm, analogical modeling, probably approximately correct (PAC) learning, ripple down rules, a knowledge acquisition methodology, symbolic machine learning algorithms, subsymbolic machine learning algorithms, support vector machines, random forests, ensembles of classifiers, bootstrap aggregating (bagging), boosting (meta-algorithm), ordinal classification, regression analysis, information fuzzy networks (IFN), statistical classification, linear classifiers, fisher's linear discriminant, logistic regression, perceptron, support vector machines, quadratic classifiers, k-nearest neighbor, hidden Markov models and boosting. Some non-limiting examples of unsupervised learning which may be used with the present technology include artificial neural network, data clustering, expectation-maximization, self-organizing map, radial basis function network, vector quantization, generative topographic map, information bottleneck method, IBSEAD (distributed autonomous entity systems based interaction), association rule learning, apriori algorithm, eclat algorithm, FP-growth algorithm, hierarchical clustering, single-linkage clustering, conceptual clustering, partitional clustering, k-means algorithm, fuzzy clustering, and reinforcement learning. Some non-limiting examples of temporal difference learning may include Q-learning and learning automata. Another example of machine learning includes data pre-processing. Specific details regarding any of the examples of supervised, unsupervised, temporal difference or other machine learning described in this paragraph that are generally known are also considered to be within the scope of this disclosure. Support vector machines (SVMs) and regression are a couple of specific examples of machine learning that may be used in the present technology.

In some examples, the machine learning module 122 may include access to or versions of multiple different machine learning models that may be implemented and/or trained according to the techniques described herein. For example, the machine learning model may be trained using annotated video data of patient care facilities, object detection models, pose estimation standard models, and/or synthetic data using 3D models. Any suitable machine learning algorithm may be implemented by the machine learning module 122. For example, machine learning algorithms can include, but are not limited to, regression algorithms (e.g., ordinary least squares regression (OLSR), linear regression, logistic regression, stepwise regression, multivariate adaptive regression splines (MARS), locally estimated scatterplot smoothing (LOESS)), instance-based algorithms (e.g., ridge regression, least absolute shrinkage and selection operator (LASSO), elastic net, least-angle regression (LARS)), decisions tree algorithms (e.g., classification and regression tree (CART), iterative dichotomiser 3 (ID3), Chi-squared automatic interaction detection (CHAID), decision stump, conditional decision trees), Bayesian algorithms (e.g., naïve Bayes, Gaussian naïve Bayes, multinomial naïve Bayes, average one-dependence estimators (AODE), Bayesian belief network (BNN), Bayesian networks), clustering algorithms (e.g., k-means, k-medians, expectation maximization (EM), hierarchical clustering), association rule learning algorithms (e.g., perceptron, back-propagation, hopfield network, Radial Basis Function Network (RBFN)), deep learning algorithms (e.g., Deep Boltzmann Machine (DBM), Deep Belief Networks (DBN), Convolutional Neural Network (CNN), Stacked Auto-Encoders), Dimensionality Reduction Algorithms (e.g., Principal Component Analysis (PCA), Principal Component Regression (PCR), Partial Least Squares Regression (PLSR), Sammon Mapping, Multidimensional Scaling (MDS), Projection Pursuit, Linear Discriminant Analysis (LDA), Mixture Discriminant Analysis (MDA), Quadratic Discriminant Analysis (QDA), Flexible Discriminant Analysis (FDA)), Ensemble Algorithms (e.g., Boosting, Bootstrapped Aggregation (Bagging), AdaBoost, Stacked Generalization (blending), Gradient Boosting Machines (GBM), Gradient Boosted Regression Trees (GBRT), Random Forest), SVM (support vector machine), supervised learning, unsupervised learning, semi-supervised learning, etc. Additional examples of architectures include neural networks such as ResNet50, ResNet101, VGG, DenseNet, PointNet, and the like. For example, the machine learning models may include models for object recognition, pattern recognition, wave recognition, optical flow analysis, person identification, movement identification, and the like for measuring PPG and BCG and using the PPG and BCG measurements to calculate PTT.

In some aspects, there may be a calibration step prior to image analysis. Such a calibration step may be accomplished using any conventional means. For example, an oscillometer, oscillation, or wrist monitor may be used to calibrate the blood pressure of a specific patient prior to processing the image. Such calibration may be done independently or in conjunction with image analysis. For example, blood pressure may be conventionally measured at the same time or close to the time in which an image is acquired. In other aspects, blood pressure may be conventionally measured at the time of admission to a health care facility. The results of the conventional measurement may be input into the patient monitoring system 114 and images may be analyzed to compare the conventional measurement and the calculated blood pressure. If there is a statistical difference between the blood pressure as calculated and the blood pressure as measured, the patient monitoring system 114 is re-calibrated. Such calibration may additionally allow for consideration of variability between individuals. In some aspects, cuff-based measurements may be used in combination with imaging to determine PTT. In some aspects, the calibration step may include inputting patient specific data such as for example, known disease states, injuries, or other aspects that may interfere with the accuracy of the measurement of the data. In some aspects, specific points on the patient that have a good correlation with cuff measurements may be identified.

The imaging device 102 may collect single images, series of images, or sets of images that may be partitioned into discrete points in time or analyzed as a whole. In some aspects, the images acquired from each time point may be compared to each other using patient monitoring system 114. Such a comparison may be used to detect the rate of vibration or other movement at specific location(s) on the patient. For example, micromovements may be captured by determining the difference between an area of a patient in a first image of a first capture point at a first time and a second image at the first capture point at a second time. The time between micromovements or the time to complete a micromovement may be calculated. For example, images may be analyzed to identify movements between 5 and 30 Hz, or any fraction thereof at a selected capture point. Such micromovements may be used to calculate BCG. In some aspects, measurements may be taken by analyzing wave patterns such as "I", "J", and "K" waves. In some aspects, the timing between separate capture points may be calculated. In other aspects, changes in light reflection and or absorption at capture point(s) may be identified between images at different time points. The various measurements at different capture points and combinations of BCG and PPG may be used to calculate PTT. That is, the two or more capture points used to calculate PPT may use PPG to PPG, BCG to PPG, PPG to BCG, or BCG to BCG measurements. Thus, there are a series of options to calculate transit time and different modalities may be used to capture the information using the same or different capture points chosen using dynamic selection. Each capture point may be dynamically selected based on a variety of features including the quality of the image capture. The selected capture point may be used to determine BCG, PPG, or both.

In some aspects, the images may be analyzed to determine a difference in a reflection from a capture point at a first point in time and the reflection from a capture point at a second point in time. The reflection may be from a retroreflective surface applied to the patient or from the skin of the patient.

In some aspects, the reflection may be used to directly capture the micromovement at the capture point in comparison to previous frames. In other aspects, the angle of incidence and the angle of reflection may be computed to locate a secondary region of interest where the reflection of a patch at a capture point(s) will be observed. For example, a secondary region of interest may be a location other than a capture point where a reflection may be observed, for example the ceiling, wall, bedrails, or any other surface. Once located, the movement will be observed by tacking the reflection of n the secondary region of interest. Using the secondary region of interest, the movement may be calculated using the signal to noise ratio to determine the BCG measurement.

Figure 5A:
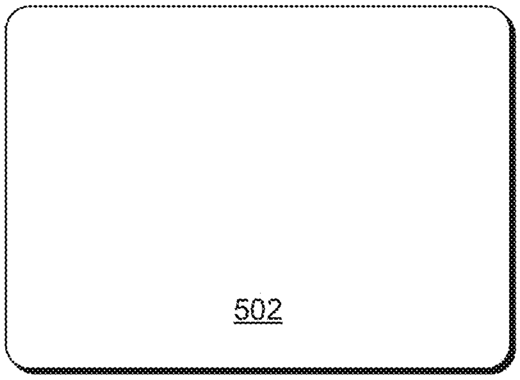
FIGS. 5A-5C illustrate a wearable patch that may be used on a patient according to an embodiment.
Figure 5B:
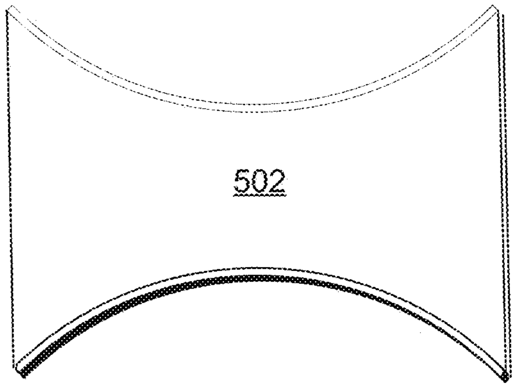
Figure 5C:
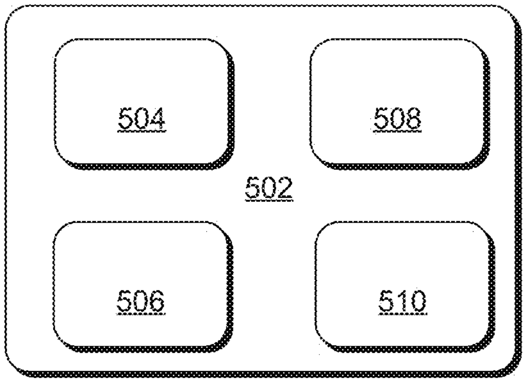

In some aspects, a patient may be wearing a deformable device with one or more optical filters such as, for example, the devices of FIGS. 5A-5C. Changes to the signal to noise ratio in images captured using such filters may enhance the $Hb/HbO_2$ contrast. Images at a first time point and images at a second time point may be compared to determine changes in $Hb/HbO_2$ which may be used in a PPG reading.

As patients rarely lie still, the imaging capture module 116 may dynamically select the capture points from which measurements will be made at any given point in time. For example, if a desired capture point is covered by clothing or other fabric, the system may dynamically select an alternate capture point that is more visible. In some aspects, the system may evaluate the illumination of any single capture point and use the amount of illumination in conjunction with the visibility of the capture point to dynamically select an appropriate capture point. Capture points used for measuring BCG and PPG may be the same or different. In some aspects, information from multiple capture points may be used.

Additionally, the machine learning module 122 may analyze the images to identify the position of the patient 108. The position or orientation of the patient may be determined via image analysis or using one or more reference points on the patient. Such reference points may be preexisting reference points such as the edge of a sheet or piece of clothing, or created reference points such as through the use of a patch or other item of a known shape, size, and orientation. Exemplary methods for dynamically selecting capture points are shown in more detail in reference to FIG. 3.

To monitor blood pressure, heartbeat related movement at identified capture points may be captured via imaging device 102. In some aspects, images may be captured at one or more locations on the body at one or more points in time. In some aspects, a plurality of imaging devices 102 may be used to capture different parts of the body. In other aspects, multiple capture points may be analyzed from the same image. For example, portions of an image or set of images may be cropped to isolate each capture point and each capture point may be analyzed separately. In other aspects, the image in its entirety may be analyzed.

In some aspects, the images may be analyzed to provide measurements at one or more locations or capture points on the body. In some aspects, measurements may be taken at points that are the furthest apart, for example, one foot to another foot, one foot to an arm on the other side of the body, or from the heart to a radial point such as an arm or a peripheral point such as a foot. This distance is not based on exterior, but on interior dimensions. That is, if the hand is over the heart, the distance to the heart is not zero, but the distance of the vasculature path, that is, the distance from the hand through the arm, across the shoulder, and down the chest to the heart. Further, the position of the capture points relative to gravity may be determined. That is, if the wrist is above the heart, below the heart, or on the heart, that information may be captured and input into the patient monitoring system 114.

The BCG and PPG measurements may be used to calculate pulse transit time (PTT). A comparison of the PTT between a plurality of locations may provide information regarding the state of the body as a whole. For example, a comparison of the pulse transit time between the heart and the right arm and the heart and the left arm may identify a possible aneurysm, blockage, stenosis, atherosclerosis, peripheral artery disease, coarctation, dissection, or other intra- and extra-arterial obstruction. Comparisons may additionally be relevant for individuals with heart disease (atherosclerosis), kidney disease, and diabetes (peripheral artery disease). Comparison of pulse transit time between other locations may identify additional conditions or adverse health events. For example, in shock, the peripheral blood flow constricts, resulting in faster pulse transit time. Thus, if the system detects an increase in pulse transit time, or a pulse transit time that is higher than a reference level, a caregiver may be alerted. Other conditions may result in vasodilation and thus slower pulse transit time in comparison to the patient at a different point in time or in comparison to a reference level. A reference level may be obtained from the same patient or a different patient or population of patients. Such a different patient or population of patients may be generic or may be age/sex/disease matched to the patient being monitored.

During image processing, the rate of movement of the patient's body at a first capture point and the rate of movement of the patient's body at a second capture point may be compared, and pulse transit time (PTT) calculated. Pulse Transit Time (PTT) is the time it takes a pulse pressure waveform (a signal that shows the variation in blood pressure in the body's arteries) to propagate through the arterial tree. The pulse pressure waveform is generated by the ejection of blood from the left ventricle and moves with a velocity much greater than the forward movement of the blood itself. In some instances, measurements may be taken from a foot to an arm, from the left to the right arm, from the heart to a foot or an arm, or the relative pulse transit time may be otherwise calculated. In other aspects, measurements may be between the heart and a peripheral pulse site. For example, the pulse may be analyzed at various locations of the upper and lower extremities, including the radial, brachial, femoral, popliteal, posterior tibial, and *dorsalis* pedis arteries. The pulse may additionally be analyzed at points such as the carotid and temporal arteries. Different observations may be made depending on the rate, rhythm, intensity, and symmetry of the pulse. For example, if the PTT is different on the left side in comparison to the right side, that may be an indication of a blockage, aneurysm, aortic dissection, stenosis, or other adverse health event.

In one example, an RGB camera may detect skin movement changes at specific capture points of the patient 108 over a period of time and use image processing techniques to yield a BCG for patient 108. In other examples, an IR camera may be used. In some aspects, PPG measurements may be taken using transdermal optical imaging techniques. In some aspects, changes in pixel intensity may be measured to determine BCG and/or PPG measurements. The BCG and PPG measurements may be used to calculate PTT which is then used to determine blood pressure using blood pressure calculation module 125. In some aspects, a difference equivalent to 10 mmHg or greater between one location and the other may trigger an alert to be sent to the clinician device 128.

In some aspects, image capture may be enhanced via one or more wearable patches such as the patches shown in FIGS. 5A-5C. The one or more wearable patches may be attached to a patient 108 using an adhesive. In some aspects, the patches may have a known size, shape, and orientation. Thus, the location of the patch may provide a reference to determine the position of the body. In some aspects, the patch magnifies movement, allowing for more precise measurements to be acquired via the imaging device 102. The patch may be rigid or deformable. For example, if a rigid patch is used, the movement of the patch in response to the pulse at the capture point may be captured by the imaging device 102. If the patch is deformable, the deformation and/or movement may be captured by the imaging device 102. The deformation may be mechanical, thermal, or optical. Optical signals may be visible or invisible to the human eye. In some aspects, the patch may be a retroflector, an elastomeric compound that changes as it mechanically moves about the patient, a bistable capacitor, or the like. For example, the patch may be an elastomeric closed cell foam colored to be responsive to a micromovement at the skin of the patient indicating the pulsatile beat. In some aspects the patch may be bistable, producing a visible change in state in reaction to heartbeat dependent micromovements. For example, the patch may be patterned such that the pattern alters in response to the rhythm of the pulse. In some aspects, the patch may include one or more conductive elements (e.g., plates) that exhibit different electrical characteristics, such as capacitance in response to elongation, bending (e.g., a bending radius), and/or other forms of deformation in response to the rhythm of the pulse. In some aspects, the patch may be colored such that the hue or tone of the color changes depending on the deformation.

The reflection or other changes may be captured by the imaging device. In some aspects, the system 114 may analyze images captured at one or more points in time. Such a comparison may be used to determine changes in body position as well as changes at a capture point between images, for example, a micro-movement or change in blood flow related to the pulse or heartbeat at a capture point.

In some aspects, the patch may include a light-emitting apparatus. The light may be designed to direct and enhance the mechanical movements captured at a surface of the patient 108. In other aspects, the patch has a passive retroreflective surface. Illumination emanating from an illumination device may be sent to the passive patch and returned, allowing for movement of the patient due to heartbeat to be observed in the intensity variations of the returned signal. For example, a patch such as patch 502 mechanically coupled to a patient may enhance movement resulting from a heartbeat. In some aspects, a plurality of patches may be placed on important landmarks of the body of the patient such as the capture points shown in FIG. 2, enhancing the capture of movement at multiple locations of the body. In some aspects, the patch may include an optimized light-emitting apparatus. The image capture module 116 may measure dimensions such as the intensity, distribution, and location of a representative pixel area. The representative pixel may be automatically selected or may be determined based on the quality of the image. For example, a representative pixel area may be hundreds or thousands of pixels per unit area. In some aspects, the representative pixel area may be a patch on the patient or the dimensions of an identified capture point. Such dimensions may be used to measure the rate of change or movement at the one or more capture points over a span of time.

In some aspects, the patches may have regions with different attributes. For example, a first region of a patch may be designed to relay the maximal mechanical return signal to obtain BCG. Other regions may be designed to relay other information. For example, regions of the patch may include one or more optical filters. In some aspects, the filter(s) may enhance contrast between variations in movement, or contrast between components in the observable region. For example, in some aspects, such filters may enhance $Hb/HbO_2$ contrast to determine PPG. In some aspects, the filter may be a low or high pass design with a pass point at 800 nm or 770 nm.

In some aspects, the patch may be combined with an active illumination system of a known wavelength and frequency. This allows for mitigation of interference from other lights in the room as light of a specific wavelength is returned to the camera. In some aspects, the illuminator may have a corresponding spectral characteristic that is mapped to the filter on the patch, for example, 686 nm for a red filter. Such an illumination system may be color-calibrated to illuminate a region of interest designated for observation such as a cheek, finger, or toe among others.

In some aspects, patient monitoring system environment 100 may include additional means of amplifying or further differentiating objects or actions within the image(s). These techniques or means may be used alone or in combination with the patch or other enhancement devices. For example, in some aspects, the illumination system may be used to eliminate background light. In some aspects, images may be acquired by the imaging device 102 both with the illumination system and without the illumination system. In some aspects, the image processing system may subtract the first image or set of images from the second image or set of images, removing background light. In some aspects, this is done every other frame or otherwise episodically such that periodic changes in background light are removed from the image analysis. In some aspects, an image histogram may be produced and used to identify illumination differences between the first image or sets of images and a second image or set of images.

In some aspects, the frame rate of the imaging system may vary depending on the information being captured. In some aspects, images may be captured as sets of images. For example, an average video capture rate may be 28 frames, per second, but a higher capture rate may be used or may be dynamically changed depending on what is being captured. For example, if the micromovement being captured is between 0.1 Hz to 30 Hz, the frame rate may be adjusted accordingly. In some aspects, the PPG frequency ranges is between 0.5 to 5 Hz. In some aspects the BCG frequency range is between 5 to 20 Hz. The minimum frame rate may be adjusted to encompass the BCG frequency, the PPG frequency, or both.

In some aspects, the frame rate for various levels of illumination may be the same or different. For example, a frame rate at a first level of illumination may be 30 frames/second. A second set of images may be acquired at a second level of illumination at a frame rate of 30 frames/second. Thus, the aggregate frame rate would be 60 frames/second. For imaging using patches with multiple filters, there may be differing types as well as different quantities of illumination. For example, a first set of images with no additional illumination may be captured at a rate of 30 frames/second. A second set of images may be captured at a frame rate of 30 frames/second using illumination at a first wavelength. A third set of images may be captured at a frame rate of 30 frames/second using illumination at a second wavelength. The collective set of images is then processed using the first set of images or a histogram of the first set of images to remove the background light from the second and third sets of images and calculating changes between the second and third sets of images using dimensions such as the intensity, distribution, and location of a representative pixel area to measure the rate of movement. Such dimensions may be used to measure the rate of change or movement at the one or more capture points. Further, such images may provide the ratio of $Hb/HbO_2$ for the second and/or third sets of frames.

Measurements acquired from the images may be sent to or requested from a clinician device 128. In some examples, the clinician device 128 may include a computing device such as a mobile phone, a tablet computer, a laptop computer, a desktop computer, and so forth which may provide a clinician (e.g., a doctor, nurse, technician, pharmacist, dentist, etc.) with information about the health of the patient 108. In some cases, the clinician device 128 may exist within a healthcare establishment, although examples are also considered in which the clinician device 128 exists and/or is transported outside of a healthcare establishment, such as a doctor's mobile phone or home desktop computer that the doctor may use when the doctor is on-call. In some examples, the clinician device 128 may include a processor, microprocessor, and/or other computing device components, shown and described below.

In some examples, the patient monitoring system 114, the imaging device 102, and/or the clinician device 128 may generate, store, and/or selectively share signals, imaging data, sensor data, and/or other patient data between one another to provide the patient and/or clinicians treating the patient with improved outcomes by accurately monitoring the patient characteristics and alerting clinicians when a change in the characteristics of the patient may indicate that the patient is in need of caretaker intervention.

Example configurations of one or more of the imaging device 102, an optional patch, an illumination device 132, a clinician device 128, and image analysis using the patient monitoring system 114 and methods for their use, are shown and described with reference to at least FIGS. 2-8 below.

Figure 2:
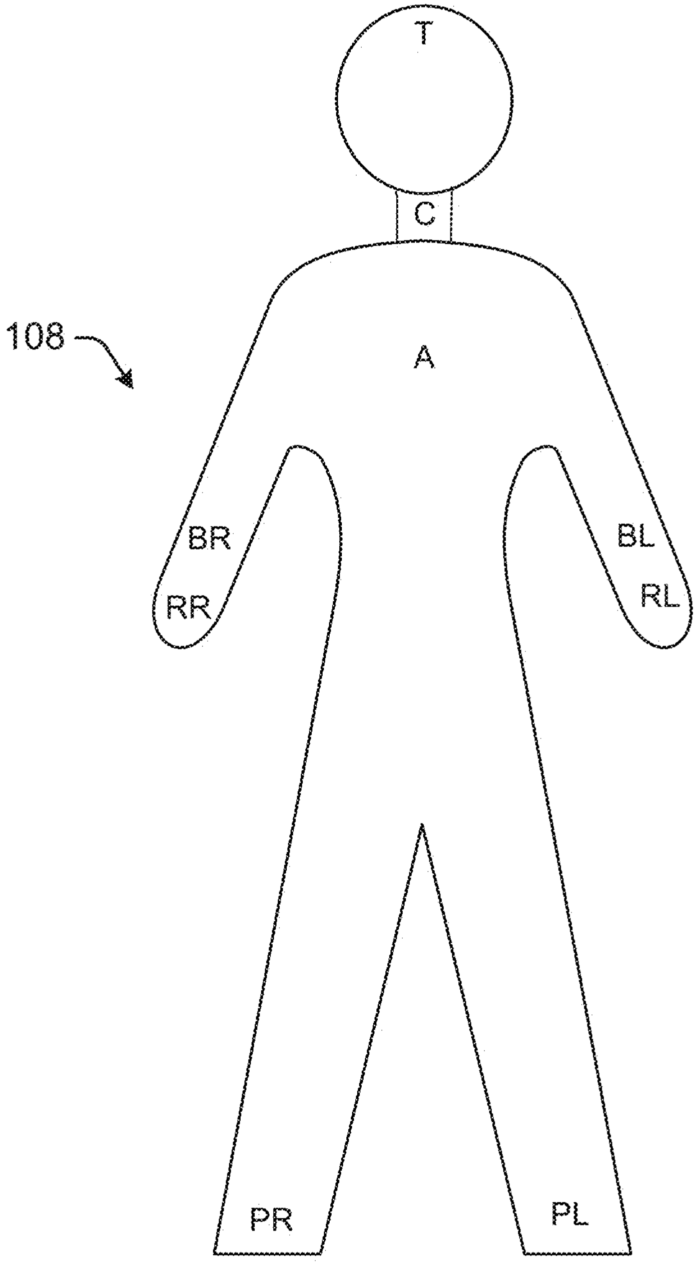
FIG. 2 illustrates prospective locations (capture points) for acquiring ballistocardiography (BCG) and photoplethysmography (PPG) readings from a patient as viewed from the camera according to an embodiment.

As shown in FIG. 2, BCG and PPG may be captured at one or more locations on the body of a patient 108 including temporal (T) and carotid (C) points. While nine capture points are shown in FIG. 2, image(s) may be analyzed to acquire measurements from as many capture points as would be useful. For example, image(s) may be analyzed to acquire measurements from one, two, three, four, five, six, seven, eight, nine, ten, eleven, twelve, thirteen, fourteen, or more sites, each of which may have a patch as discussed in further detail with reference to FIGS. 5A-5C or may be imaged without a patch. In some aspects, a single image or set of images including a video stream is analyzed to acquire heartbeat movement measurements from each location. In other aspects, different images from one or more cameras are analyzed to acquire movement measurements more generally. In some aspects, one or more images may be analyzed to capture the ratio of oxygenated to deoxygenated blood. In other aspects, one or more images may be analyzed to capture changes in perfusion at the capture point.

Using measurements from the capture points, a variety of conditions can be assessed including arrhythmia or atherosclerosis, to name a few. For example, if the radial pulse is lower than the apical pulse, a pulse deficit may be detected, indicating an arrhythmia. Such a determination may be made by comparing BCG at apical (A), and BCG at radial left (RL) or radial right (RR). In another example, PPG may be captured at each site using optical transmission. PPG and BCG may then be combined to calculate pulse transit time (PTT). Peripheral artery disease such as atherosclerosis may be identified by calculating PTT and comparing blood pressure differences at different sites such as the PTT from A to RR, PTT from A to RL, PTT From A to peripheral right (PR), and PTT from A to peripheral left (PL). PPG and BCG may be acquired from the same or different capture points in each image or sets of images. In some aspects, each of PPG and BCG may be captured using different capture points in each image or set of images. For example, in a first set of images of a first capture point may be used and in a second set of images at a second, different capture point may be used to acquire the PPG and BCG data. The specific location such as A, RL, RR, PR, and PL to be used may be determined through image analysis. In some aspects a capture point may be determined, for example, using the dynamic selection process shown in FIG. 3.

Figure 3:
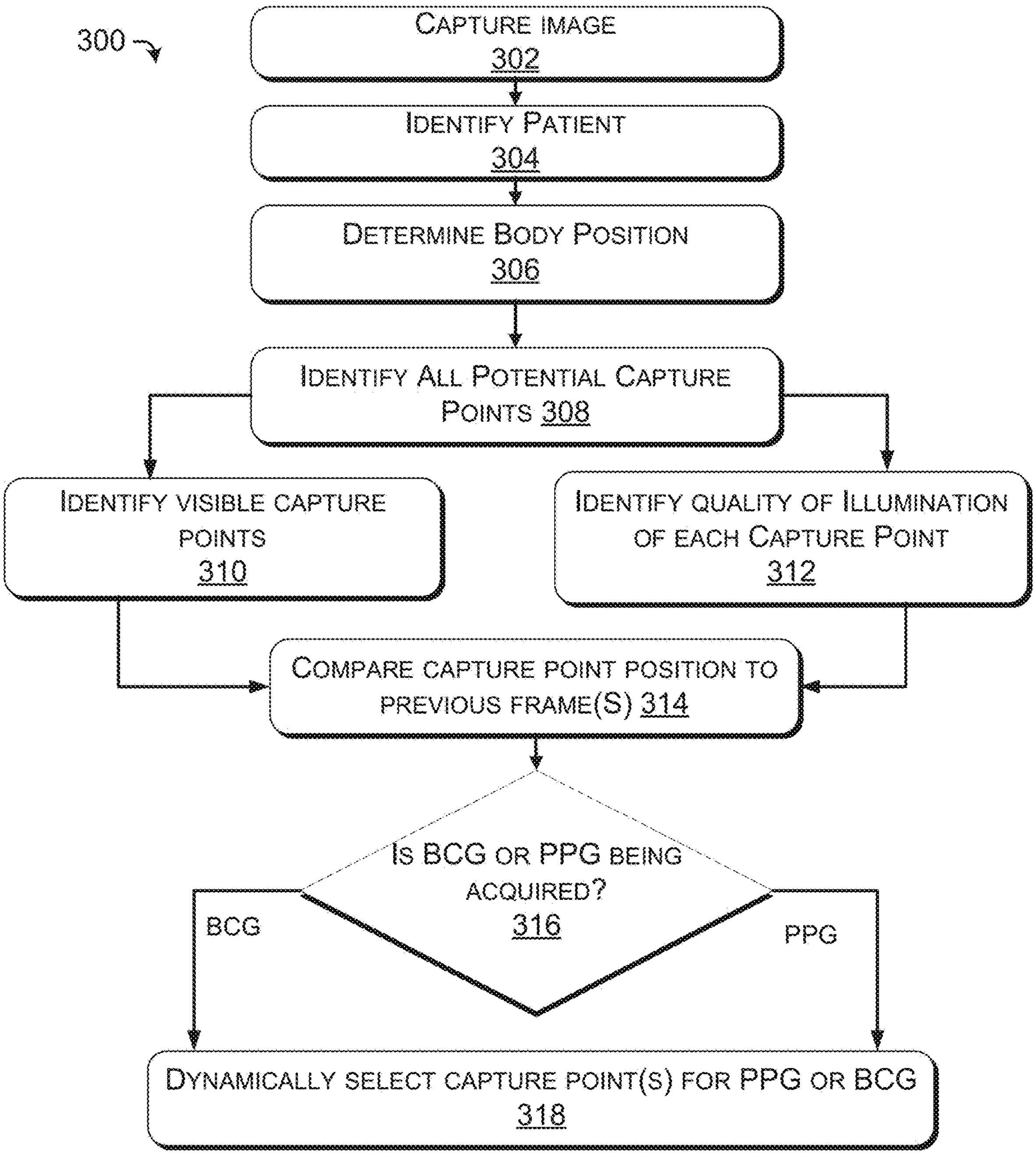
FIG. 3 illustrates a process for dynamically selecting capture point(s) for acquiring PPG and BCG readings according to an embodiment.

As shown in FIG. 3 in process 300, capture points are dynamically selected. At 302, an image is captured using an imaging device such as imaging device 102. The image is then analyzed to identify the patient at 304. Patient identification may be accomplished using, for example, one or more modules from patient monitoring system 114 such as image capture module 116 and/or object identification module 124. The patient may be identified using any means generally used by those of ordinary skill in the art. For example, a patient may be identified by using facial recognition software or by scanning a wristband or other identification attached to the patient.

Once the patient is identified at 304, the body position of the patient is determined at 306. In some aspects, body position is determined using object identification module 124. Body position may be determined, for example, using human pose estimation including kinematic, planar, and volumetric pose estimation to identify the location of specific key points like hands, head, elbows, etc. In other aspects, body position is determined using a reference point such as the edge of a sheet, shirt, or a patch of known size, shape, and orientation. Once the patient's body position is identified, all potential capture points for that patient are determined at 308. The image is then analyzed to identify visible capture points at 310 and evaluate the quality of the illumination at each capture point at 312. Each visible capture point in an image frame may then be compared to the same respective capture point in a previous frame or set of frames at 314 to determine whether the body position has changed. For example, if the capture point is the wrist and in one set of frames the wrist is s at the waist and in another set of frames the wrist is overhead, the wrist may be a less useful capture point for comparison purposes.

The process 300 then identifies whether the image is being analyzed for BCG or PPG measurements at 316. If BCG is being acquired at 316, the system identifies the best capture point(s) for BCG at 318 and extracts the BCG at the capture point with the highest fidelity. If PPG is being acquired, the system may evaluate changes in illumination to determine the capture point(s) to be used. While a change in illumination may be identified by any means generally used, in some aspects an intraframe histogram may be produced. In some aspects, the intraframe histogram is of the entire image. In other aspects, the intraframe histogram is of a region of interest such as, for example, a capture point, or a region immediately adjacent a capture point.

For example, a histogram may be produced for each potential capture point at each timepoint. The information in a histogram from a prior frame or set of frames is then subtracted from the histogram produced from the current frame or set of frames to determine a change of illumination at the capture point(s) of interest. Such comparisons may be between serially acquired by not necessarily contiguous time points. A change in illumination such as a light being turned on or off or a person walking between the illumination source and the patient may then be identified, allowing for correction of the reflective reading for PPG or selection of a different capture point. In some aspects, the signal to noise ratio of a capture point may be analyzed. The system then dynamically selects a capture point with the highest fidelity for PPG at 318. The process 300 then uses the information obtained from the capture points to determine BBG or PPG and uses BBG and PPG to calculate pulse transit time and blood pressure as shown FIGS. 7 and 8. The process 300 may then repeat. In some aspects, image capture is episodic or periodic. In other aspects, image capture is continuous or near continuous.

Figure 4:
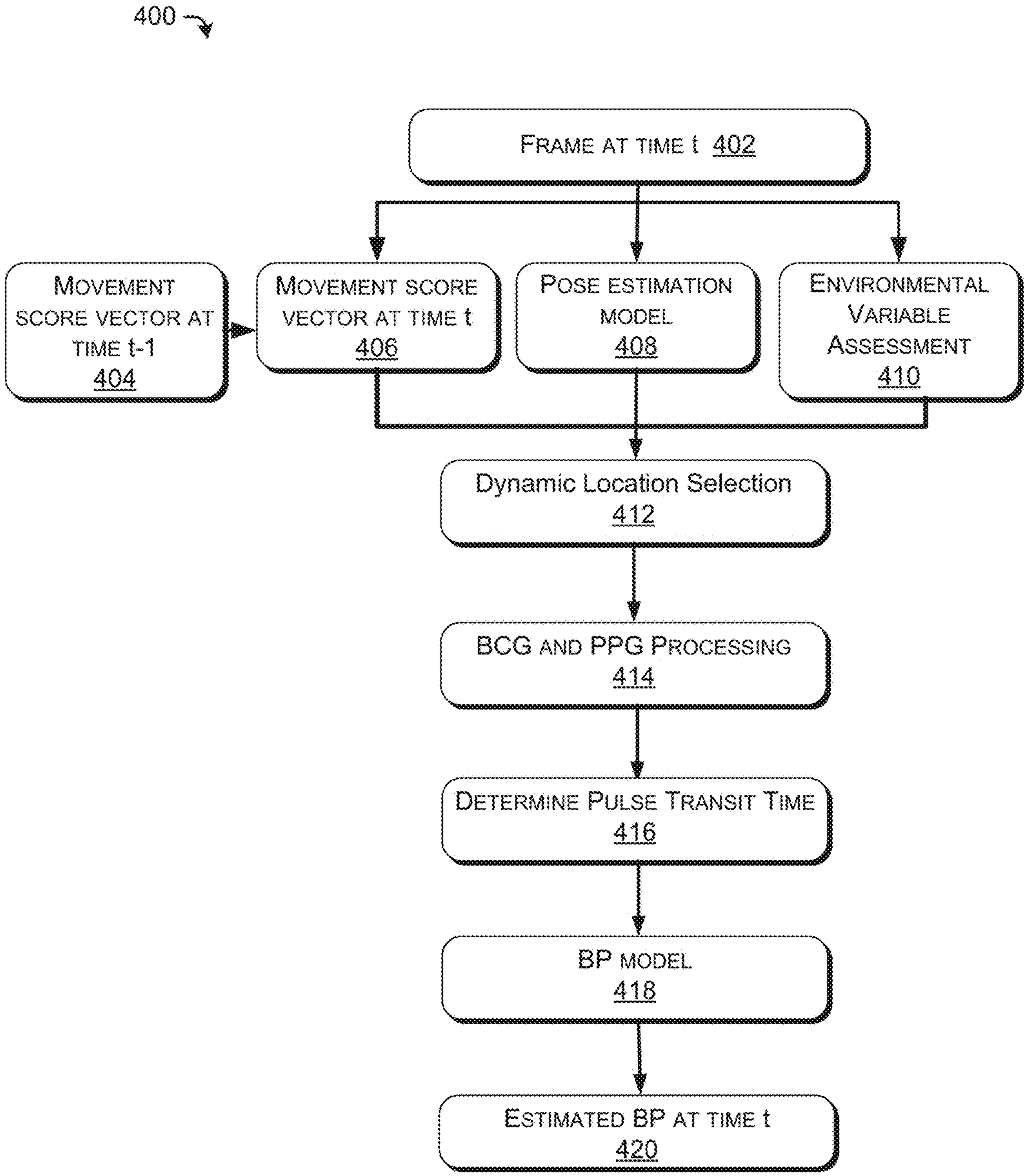
FIG. 4 illustrates a process for determining blood pressure according to an embodiment.

As shown in FIG. 4 in process 400, the identification of which image or portion of an image is to be analyzed may depend on the position of or movement by the patient. For example, at time t at 402, a frame of an image is selected. A movement score is assigned to an image taken at time t-1 at 404 and to the image taken at time t at 406. The image may be analyzed using a pose estimation model 408 to determine the relative position of the capture point to the heart. For example, if a limb is located over the head of the patient or is in an unsupported position such as dangling off of the side of the bed, the system may determine that those capture points are less useful than other capture points. Environmental variable assessment 410 may include obstructions of a capture point such as a cover or item of clothing over a capture point, changes in lighting, movement, and the like. In some aspects, it may be determined that something, for example, an individual such as a caregiver, may be moving across the capture path to acquire the capture point, decreasing the desirability of a particular capture point. Information from the movement scores 406, the pose estimation model 408, and the environmental variable assessment 410 are combined and analyzed using patient monitoring system 114 to dynamically select the location(s) on the patient, that is, the capture point(s), to be analyzed at 412. For example, the movement score may be calculated by comparing multiple frames over time. In some aspects, the movement score may include a variable assessment, that is it may identify that the patient has moved between a first frame and a second frame. Such movement may impact the reflected light that may be captured such that the system may determine that a different capture point should be used, for example using dynamic location selection as shown for example in FIGS. 3, 7, and 8.

Sites used for BCG and PPG measurements may be the same or different and may be independently dynamically selected to obtain the clearest signal. Dynamic selection may consider, for example, whether the selected capture point is occluded or visible, non-moving, well-lit, and/or associated with a supported body structure, that is, not free-standing using information from the environmental variable assessment 410.

After a capture point is selected, the remaining points may be ranked to provide the best possible path selection for the second measurement point and the measured BCG and PPG may be pre-processed at 414. PTT may be calculated between a specific point in the heartbeat to a specific location using BCG and PPG measurements. The system may track each different timing and the capture point may be identified based on the clearest signal for either BCG and/or PPG. The PPG measurement is a spectral change reflective of blood volume and the BCG measurement is of a mechanical change reflective of movement due to a heartbeat. Calculation of PPT may be based on measurements taken for either or both BCG and PPG. That is, the two capture points used to calculate PPT may use PPG to PPG, BCG to PPG, PPG to BCG, or BCG to BCG measurements. Thus, there are a series of options that may be used to calculate pulse transit time at 416 and different modalities may be used to capture the information using the same or different capture points chosen using dynamic selection.

Pulse transit time is the time interval required for a pressure wave to travel between two sites in the arterial tree. It may be estimated using, for example, a BCG signal and a PPG signal, but detecting landmarks within the BCG signal such as the I, J and K wavers and/or the PPG signal such as the systolic peak, the dicrotic notch, or the diastolic peak, and mearing the time between the landmarks. In some aspects, pulse transit time may be defined between the chosen capture points and may include separate measurements such as PTT_rl (pulse transit time from chest to RL), PTT_rr (pulse transit time from chest to RR) or any other set of capture points as shown, for example in FIG. 2 of the subject application The identified pulse transit time is then put into the machine learning blood pressure (BP) model at 418 to estimate the blood pressure at time t at 420.

As described with reference to FIGS. 5A-5C, the system may use one or more patches attached to a patient using, for example, an adhesive. In some aspects, a patch such as patch 502 may be deformable such that movements by the patient are mirrored in the patch, allowing for amplified movement to be captured by the imaging device 102. In some aspects, patch 502 may be used by the imaging device 102 as a reference point, that is, as the location of the patch on the body is constant and the shape, size, and orientation of the patch are known, the imaging device 102 or image preprocessing module 120 may use the patch as a marker to identify relative positioning of objects such as the patient or portions of the patient within the image as identified by object identification module 124. In some aspects, the patch may be retroreflective, increasing the visibility of any movement.

As shown in FIG. 5B in comparison to FIG. 5A, the patch 502 may be deformable. Such deformation may be used to indicate the rhythm of the pulse, or the waveform being sent by the heart. In some aspects, the patch may be mechanically deformable as shown in FIG. 5B, that is as a pressure wave created cardiac cycle moves through, the patch 502 may change to reflect the pattern of the movement. The deformation may be mechanical, optical, thermal, or a combination thereof. In some aspects, the change may be detected using the imaging device 102. In some aspects, the change may be detected optically by using visible or invisible waveforms, for example using radar or infrared imaging. In other aspects, the change may be detected thermally. In some aspects, the change may be a change in the state of a bistable capacitor. For example, the patch may include one or more conductive elements (e.g., plates) that exhibit different electrical characteristics, such as capacitance in response to elongation, bending (e.g., a bending radius), and/or other forms of deformation in response to the rhythm of the pulse.

As shown in FIG. 5C, in some aspects a patch 502 may have one or more regions 504-510. In some aspects, one or more of regions 504-510 is an optical filter. In some aspects, one or more of the optical filters may be transparent, allowing for information to be collected from the skin below. For example, optical filter 504 may be a green light filter; optical filter 506 may be transparent, forming a directly observable region; optical filter 508 may be a red light filter; and optical filter 510 may be an infrared light filter. In some aspects, one or more of regions 504-510 is retroreflective. Such filters may be transparent or opaque. In some aspects, they are passive filters. In other aspects, they are active filters. In some aspects, a transparent region allows for optical imaging to capture PPG. In some aspects, one or more of the optical filters enhance the $Hb/HbO_2$ contrast. For example, the optical filter may be a low or high pass design with a pass point located between $HbO_2$ and deoxygenated (De) $HbO_2$, for example at 800 nm. Patches may be placed at one or more capture points on the body as shown in FIG. 2 or FIG. 6.

FIG. 6 is a top view of a patient monitoring environment 600. An imaging device 602 and illumination device 632 are positioned on a gimbal or stand 640. The gimbal or stand 640 allows for positioning the illumination device 632 and/or the imaging device 602. In some aspects, the gimbal may mechanically tilt to position the light 632 and the imaging device 602 to the desired position. The moveable platform 640 may be configured to be steerable in at least one of an x-direction, a y-direction, or a z-direction within the care facility or other space. In some aspects, the imaging device 602 and light 632 may be positioned at a specific distance apart on the stand 640, for example, offset by 4-5 cm. In other aspects, the illumination device 632 may be coaxial with the imaging device 602. For example, the illumination device 632 may be a ring light, allowing for images to be captured through the center of the illumination device.

The imaging device 602 similar to imaging device 102 may be positioned to capture a field identified by arrows 602*a* and 602*b* including a patient 608 similar to patient 108. In some aspects, the stand 640 may be moved so that the imaging device is positioned to capture the field including the patient 608. As shown in FIG. 6, the patient may be wearing a patch 630. The patch 630 may be similar to patch 502 as shown in FIG. 5A-5C. The illumination device 632 may provide illumination to a patient and receive reflection of the light from the patient as shown by 632*a* and 632*b*. Such an illumination source may be an LED light such as an RGB LED, a full spectrum light, or other light sources. In some aspects, the illumination device may be used intermittently such that a first set of images is acquired with the illumination and a second set of images is acquired without or vice versa. In some aspects, images may be taken using different wavelengths of light. For example, a first set of images may be taken using ambient lighting, a second set of images may be taken using a second wavelength, and a third set of images may be taken using a third wavelength. Other patterns of illumination including constant illumination may also be used. In some aspects, one or more filters may be applied to the structured illumination device, for example, a polarizing filter, infrared filter, UV filter, and the like. In some aspects, illumination may be used serially. That is, a first image may be acquired using illumination device 632 and a second image may be acquired without the illumination device. Image pre-processing module 120 may then subtract the background light. In some aspects, a series of images with illuminations at different wavelengths may be captured and processed to extract different types of information such as the amount of perfusion and changes in perfusion or the amount of oxygenated to deoxygenated blood.

Figure 7:
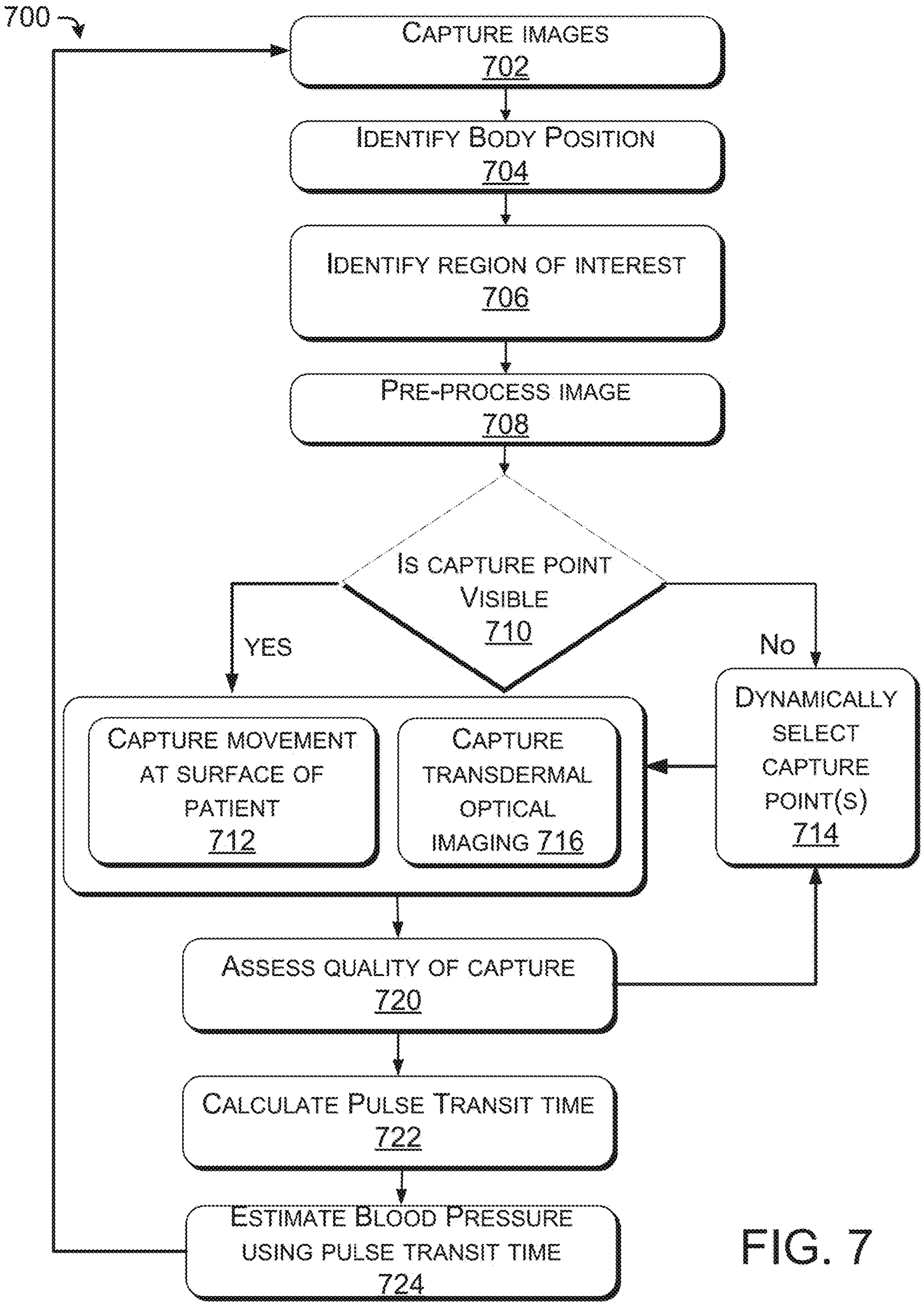
FIG. 7 illustrates a process for determining blood pressure according to an embodiment.

FIG. 7 illustrates an exemplary process 700 for calculating blood pressure. At a first step 702, an image is captured. The image may then be analyzed to identify the body position at 704. While the body position may be identified for any reason, in some aspects different body positions may impact the accuracy of readings. For example, if the limbs are above or below the heart, or if a limb is supported such as on a bed or pillow or unsupported such as dangling off of the side or raised, such as extended outside the bed, PTT readings may vary. Once the body position is determined, the image may be analyzed to identify a region of interest including a capture point at 706. The image may then be subject to pre-processing at 708 prior to analysis. For example, there may be brightness and contrast compensation, defective pixel analysis, dynamic range compression, and HDR techniques. In some aspects, pre-processing increases the suitability of the image for machine learning analysis. For example, the brightness and contrast may not yield an improved image for visual inspection but may alter the brightness and contrast on a pixel-by-pixel level, optimizing the image for analysis via machine learning. The image may then be analyzed to ensure that the capture point is visible at 710. If the capture point is not visible at 710, the system may dynamically select a different capture point at 714, ranking a series of available capture points based on one or more factors such as visibility, position, support of the limb, quality of the capture point, illumination of the capture point. In some aspects, the capture point may be dynamically selected in accordance with the method of FIG. 3. If the capture point is visible, the system captures movement at the surface of the patient 712 to extract BCG. In some aspects, the movement may be based on a comparison to the previous frame and the previous frame's capture points, for example, capture points such as those shown in FIG. 4. Optical imaging is captured at 716 to determine PPG. The system then assesses the quality of the capture at 720 using image capture module 116. If the quality of the capture does not meet threshold levels, that is, the visibility of the capture point is occluded, there is movement at the location of the capture point during image capture, there is a lighting change that impacts the quality of the image capture, the system may select a different capture point at 714. In some aspects, the capture point may be suitable for BCG capture and not PPG capture and vice versa. For example, movement may be able to be captured and used for BCG, but the quality of the illumination may be such that the $Hb/HbO_2$ contrast is insufficient. Alternatively, reflections may be visible, but the movement is occluded.

If the quality of the capture meets threshold levels, the system calculates pulse transit time at 722 by comparing differences in the surface of the patient indicative of micromovement captured at 712 and/or optical results captured at 716 indicative of changes in oxygenation between the current result and historical results of a set of previous frames. The historical results may include 1, 2, 5, 10, 15, 20, 30, 40, 50, 18, 100, 500, 1000 prior frames, or any subset thereof. Once the pulse transit time is calculated at 722, the pulse transit time may be used to estimate blood pressure at 724 using one or more models. Such models may take into consideration overall movement, patient position, pulse transit time calculated using other capture points, and the like.

Figure 8:
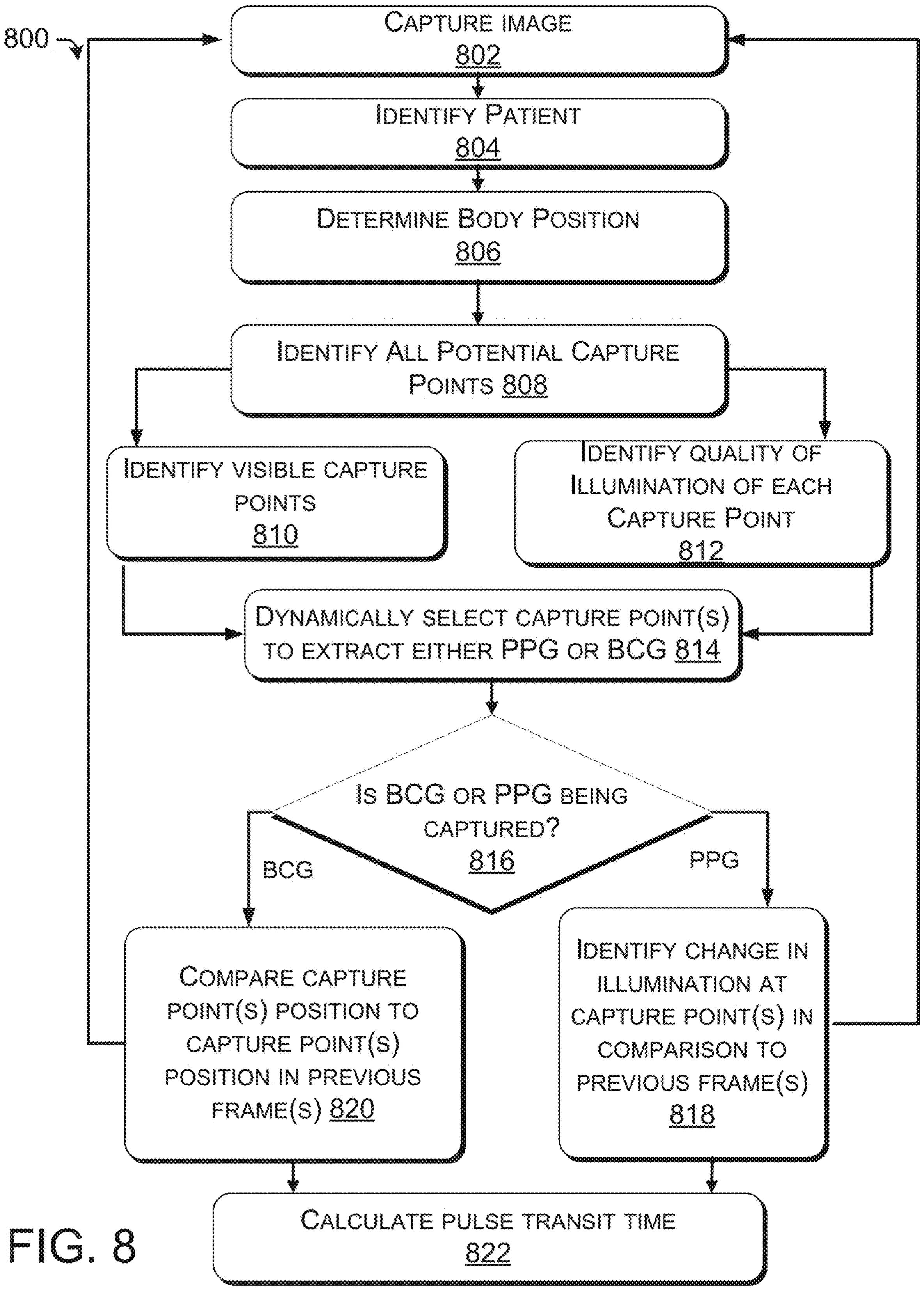
FIG. 8 illustrates a process for determining pulse transit time according to an embodiment.

FIG. 8 discloses a process 800 for calculating pulse transit time and using the pulse transit time to estimate blood pressure. At 802 an image of the patient is captured. The system then identifies the patient at 804. Patient identification may occur using a variety of mechanisms including for example, through facial recognition or scanning of an object such as a barcode on the wrist of a patient.

Once the patient is identified at 804, the body position of the patient is determined at 806. In some aspects, body position is determined using object identification module 124. Body position may be determined, for example, using human pose estimation including kinematic, planar, and volumetric pose estimation to identify the location of specific key points like hands, head, elbows, etc. In other aspects, body position is determined using a reference point such as the edge of a sheet, shirt, or a patch of known size, shape, and orientation. Once the patient's body position is identified at 806, all potential capture points for that patient are identified at 808. The image is then analyzed to identify visible capture points at 810 and evaluate the quality of the illumination at each capture point at 812.

The system may then dynamically select the appropriate capture point(s) to extract either or both PPG and BCG at 814. In some aspects, information may be captured from a plurality of capture points in a single frame. In other aspects, information from a single capture point may be extracted from each frame. The dynamic selection may consider, for example, whether the selected capture point is occluded or visible, non-moving, well-lit, and/or associated with a supported body structure, that is, not free standing. After a measurement point is selected, the remaining points may be ranked to provide the best possible path selection for the second measurement point. PTT may be calculated between a specific point in the heartbeat to a specific location using BCG and PPG measurements. The system may track each different timing and the capture point may be identified based on the clearest signal for either BCG and/or PPG. The PPG measurement is a spectral change reflective of blood volume and the BCG measurement is of a mechanical change reflective of movement due to a heartbeat. Calculation of PPT may be based on measurements taken for either or both BCG and PPG. That is, the two capture points used to calculate PPT may use PPG to PPG, BCG to PPG, PPG to BCG, or BCG to BCG measurements. Thus, there are a series of options to calculate transit time and different modalities may be used to capture the information using the same or different capture points chosen using dynamic selection.

The process then determines if BCG or PPG is being captured at 816 and each capture point(s) in an image frame is then compared to the same respective capture point in a previous frame or set of frames. If BCG is being measured, then the position of the surface of the skin at the capture point in a first frame is compared to the position of the surface of the skin in previous frames at 820. If PPG is being measured, then changes in illumination including changes in pixels or voxels in comparison to previous frames may be determined at 818. The BCG measurements and the PPG measurements may then be used to calculate pulse transit time at 822 and the pulse transit time may be used to estimate blood pressure.

Figure 9:
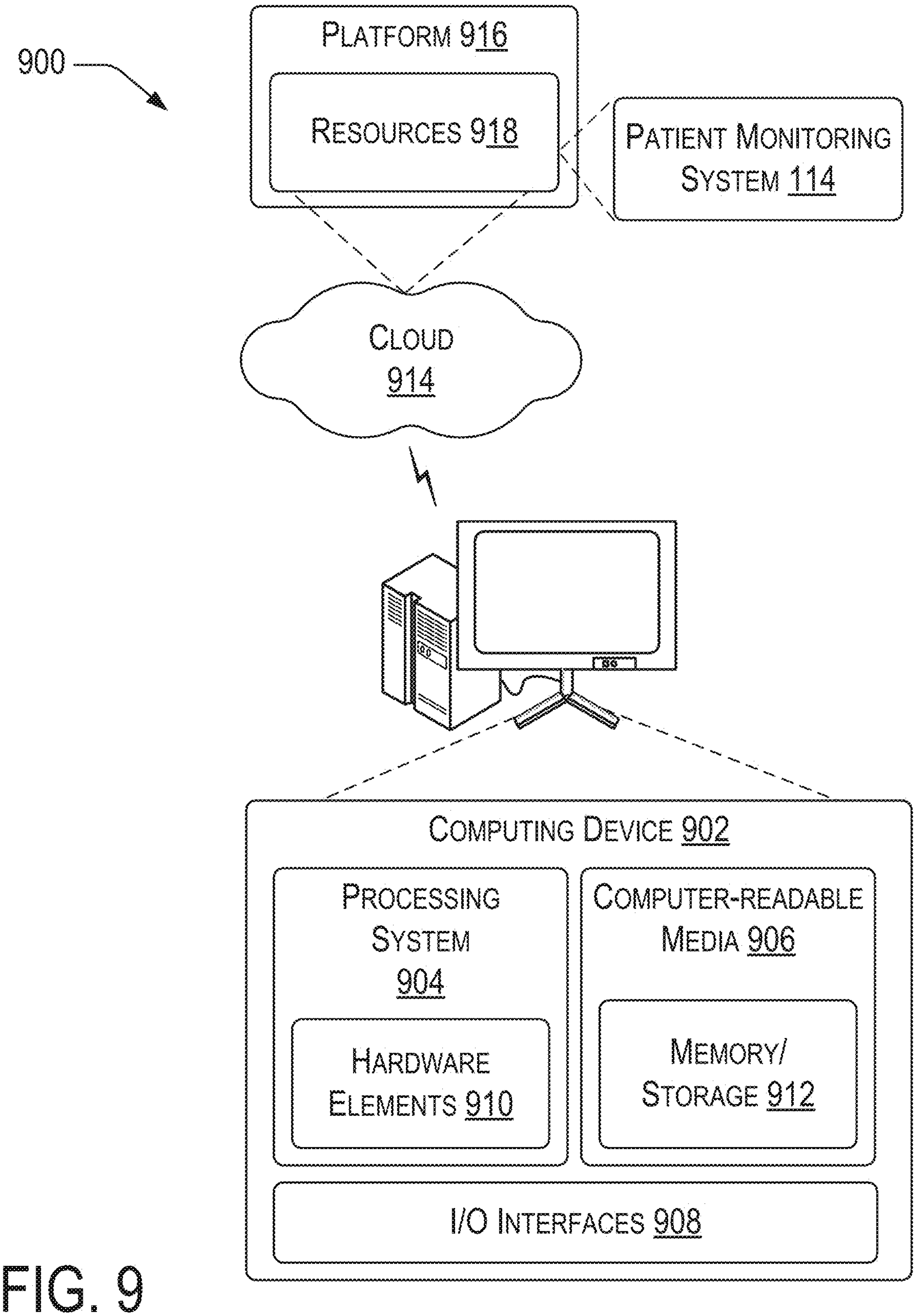
FIG. 9 illustrates at least one example device configured to enable and/or perform some or all of the functionality discussed herein.

FIG. 9 illustrates an example system generally at 900 that includes a computing device 802 that is representative of one or more computing systems and/or devices that may implement the various techniques described herein. This is illustrated through the inclusion of the patient monitoring system 114. The computing device 902 may be, for example, any type of computer or computing device generally used including a server of a service provider, a device associated with a client (e.g., a client device), an on-chip system, and/or any other suitable computing device or computing system.

The exemplary computing device 902 includes a processing system 904, one or more computer-readable media 906, and one or more I/O interface 908 that are communicatively coupled to each other. In some embodiments, the processor (s) of the processing system includes a Central Processing Unit (CPU), a Graphics Processing Unit (GPU), or both CPU and GPU, or other processing unit or component known in the art. Although not shown, the computing device 902 may further include a system bus or other data and command transfer system that couples the various components, one to another. A system bus may include one or more different bus structures, such as a memory bus or memory controller, a peripheral bus, a universal serial bus, and/or a processor or local bus that utilizes any of a variety of bus architectures. Other examples are also contemplated, such as control and data lines.

The processing system 904 is representative of the functionality used to perform one or more operations of the computing system using hardware. Accordingly, the processing system 904 may include hardware element 910 configured for example as processors, functional blocks, and the like. This may include implementation in hardware as an application specific integrated circuit or other logic device formed using one or more semiconductors. The hardware elements 910 are not limited by the materials from which they are formed, or the processing mechanisms employed therein. For example, processors may be comprised of semiconductor(s) and/or transistors (e.g., electronic integrated circuits (ICS)). In such a context, processor-executable instructions may be electronically executable instructions.

The computer-readable media 906 may include memory/storage component 912. The memory/storage component 912 represents memory/storage capacity associated with one or more computer-readable media. The memory/storage component 912 may include volatile media (such as random access memory (RAM)) and/or nonvolatile media (such as read-only memory (ROM), Flash memory, optical disks, magnetic disks, and so forth), fixed media (e.g., RAM, ROM, a fixed hard drive, and so on), and removable media (e.g., Flash memory, a removable hard drive, an optical disc, and so forth). The computer-readable media 906 may be configured in a variety of other ways as further described below.

I/O interface 908 (Input/Output interface) is representative of functionality that allows a user to enter commands and information to computing device 902, and also allows information to be presented to the user and/or other components or devices using various input/output devices. Examples of input devices include a keyboard, a cursor control device (e.g., a mouse), a microphone, a scanner, touch functionality (e.g., capacitive or other sensors that are configured to detect physical touch), a camera (e.g., which may employ visible or non-visible wavelengths such as infrared frequencies to recognize movement as gestures that do not involve touch), scanner, trackpad, joystick, stylus, and so forth. Examples of output devices include a display device (e.g., a monitor or projector), speakers, a printer, a network card, tactile-response device, hapatic feedback device, digital signage display, touchscreen, and so forth. Thus, the computing device 902 may be configured in a variety of ways to support user interaction.

Various techniques may be described herein in the general context of software, hardware elements, or program modules. Generally, such modules include routines, programs, objects, elements, components, data structures, and so forth that perform particular tasks or implement particular abstract data types as shown for example, by the flowcharts of FIGS. 3, 4, 7, and 8. The terms "module," "functionality," "logic," and "component" as used herein generally represent software, firmware, hardware, or a combination thereof. The features of the techniques described herein are platform-independent, meaning that the techniques may be implemented on a variety of computing platforms that run computer programs and applications including cloud based systems.

Implementations of the described modules and techniques may be stored on and/or transmitted across some form of computer-readable media. The computer-readable media may include a variety of media that may be accessed by the computing device 902. For example, computer-readable media may include "computer-readable storage media" and "computer-readable transmission media."

"Computer-readable storage media" may refer to media and/or devices that enable persistent and/or non-transitory storage of information. Thus, computer-readable storage media refers to non-signal-bearing media. The computer-readable storage media may include hardware including volatile and non-volatile, removable and non-removable media, and/or storage devices implemented in a method or technology suitable for storage of information such as computer-readable instructions, data structures, program modules, logic elements/circuits, or other data. Examples of computer-readable storage media may include RAM, ROM, EEPROM, flash memory or other memory technology, CD-ROM, digital versatile disks (DVD) or other optical storage, hard disks, magnetic cassettes, magnetic tape, magnetic disk storage or other magnetic storage devices, or other storage device, tangible media, or article of manufacture suitable to store the desired information and which may be accessed by a computer.

"Computer-readable transmission media" may refer to a medium configured to transmit instructions to the hardware of the computing device 902, such as via a network, for example the network(s) shown in FIG. 1. Computer-readable transmission media typically transmits computer-readable instructions, data structures, program modules, or other data in a modulated data signal, such as carrier waves, data signals, or other transport mechanisms. Computer-readable transmission media also include any information delivery media. The term "modulated data signal" means a signal that has one or more of its characteristics set or changed to encode information in the signal. By way of example, and not limitation, computer-readable transmission media include wired media such as a wired network or direct-wired connection, and wireless media such as acoustic, radio frequency (RF), infrared, and other wireless media.

As previously described, hardware elements 910 and computer-readable media 906 are representative of modules, programmable device logic, and/or device logic implemented in a hardware form that may be employed in some embodiments to implement at least some aspects of the techniques described herein, for example, to execute one or more instructions. Hardware may include components of an integrated circuit or on-chip system, an application-specific integrated circuit (ASIC), a field-programmable gate array (FPGA), a complex programmable logic device (CPLD), and/or other implementations in silicon or other hardware. In this context, hardware may operate as a processing device that performs program tasks defined by instructions and/or logic embodied by the hardware as well as hardware utilized to store instructions for execution, e.g., the computer-readable storage media described previously.

Combinations of the foregoing may also be employed to implement various techniques described herein and software, hardware, or executable modules may be implemented as one or more instructions and/or logic embodied on some form of computer-readable storage media and/or by one or more hardware elements 910. In some aspects, the computing device 902 may be configured to implement particular instructions and/or functions corresponding to the software and/or hardware modules. Accordingly, implementation of a module that is executable by the computing device 902 as software may be achieved at least partially in hardware, e.g., through the use of computer-readable storage media and/or hardware elements 910 of the processing system 904. The instructions and/or functions may be executable/operable by one or more articles of manufacture (for example, one or more computing devices 902 and/or processing systems 904) to implement techniques, modules, and other instructions described herein.

The techniques described herein may be supported by various configurations of the computing device 902 and are not limited to the specific examples of the techniques described herein. This functionality may also be implemented all or in part through the use of a distributed system, for example, through the "cloud" 914 via a platform 916 as described below.

The cloud 914 includes and/or is representative of a platform 916 for on demand resources 918. Platform 916 abstracts the underlying functionality of hardware (e.g., servers) and software resources of the cloud 914. The resources 918 may include applications and/or data that can be utilized while computer processing is executed on servers that are remote from the computing device 902, generally through third-party providers, though other remote resources may also be used. Resources 918 can also include services provided over the Internet and/or through a subscriber network, such as a cellular or Wi-Fi network, though local area networks may also be used.

Platform 916 may abstract resources and functions to connect the computing device 902 with other computing devices. The platform 916 may also be scalable to provide a corresponding level of scale to encountered demand for the resources 918 that are implemented via the platform 916. Accordingly, implementation of functionality described herein may be distributed throughout multiple devices of the system 900. For example, the functionality may be implemented in part on the computing device 902 as well as via the platform 916 which may represent a cloud computing environment.

The example systems and methods of the present disclosure overcome various deficiencies of known prior art devices. Other embodiments of the present disclosure will be apparent to those of skill in the art from consideration of the specification and practice of the disclosure contained herein. It is intended that the specification and examples be considered as examples only, with a true scope and spirit of the present disclosure being indicated by the following claims.

EXAMPLE CLAUSES

1. A method for continuous blood pressure monitoring including: receiving, by a computing device, a first set of images of a patient acquired using an imaging device; receiving, by the computing device, a second set of images of the patient acquired using the imaging device; identifying, by the computing device, a capture point visible in the first set of images and the second set of images, wherein the capture point includes a patch coupled to the patient; computing, by the computing device, a change in the patch between the first set of images and the second set of images, wherein the change is a change in pixel intensity; and computing a pulse transit time.

2. The method of embodiment 1, wherein the change in pixel intensity indicates a volumetric change of blood at a skin surface of the patient in response to a heartbeat.

3. The method of embodiments 1 or 2, wherein the patient is illuminated during acquisition of the first or second set of images.

4. The method of any of embodiments 1 to 3, wherein the patient is illuminated during acquisition of only one of the first or second set of images.

5. The method of any of embodiments 1 to 4, wherein the change in pixel intensity indicates a movement caused by a cardiac cycle.

6. The method of any of embodiments 1 to 5, further including detecting a deformation of the patch.

7. The method of any of embodiments 1 to 6, wherein the deformation is a mechanical deformation.

8. The method of any of embodiments 1 to 7, wherein the deformation is an optical deformation.

9. The method of any of embodiments 1 to 8, wherein the deformation is a thermal deformation.

10. The method of any of embodiments 1 to 9, wherein the patch is retroreflective.

11. The method of any of embodiments 1 to 10, wherein the patch includes at least one optical filter.

12. The method of embodiment 11, wherein the at least one optical filter is a red filter.

13. The method of any of embodiments 11 to 12, wherein the at least one optical filter is a green filter.

14. The method of any of embodiments 11 to 13, wherein the at least one optical filter is an infrared filter.

15. The method of any of embodiments 1 to 15, further including calculating blood pressure.

16. A system including: an imaging device located in a room; a first object located on a patient in the room; a second object located on the patient in the room; one or more processors communicatively coupled to the imaging device; and a non-transitory, computer-readable media having instruction stored thereon that, when executed by the one or more processors, cause the one or more processors to perform acts including: receiving a first set of image data captured by the imaging device at a first time point, the first set of image data representing, at least in part, the first object and the second object; receiving a second set of image data captured by the imaging device at a second time point, the second set of image data representing, at least in part, the first object and the second object; identifying a change in pixel intensity of the first object between the first set of image data and the second set of image data; identifying a change in pixel intensity of the second object between the first set of image data and the second set of image data; identifying a movement of the first object between the first set of image data and the second set of image data; identifying a movement of the second object between the first set of image data and the second set of image data; and calculating a pulse transit time based on the change in the pixel intensity of the first object and the second object and the movement of the first object and the second object.

17. The system of embodiment 16, wherein the first object and the second object are each a mechanically deformable patch.

18. The system of any of embodiments 16 to 17, wherein the mechanically deformable patch is retroreflective.

19. The system any of embodiments 17 to 18, wherein the mechanically deformable patch includes at least one optical filter.

20. The system of any of embodiments 16 to 20, wherein the first object is located proximate to the heart of the patient.

21. The system of embodiment 20, wherein the second object is located at a radial point of the patient.

22. The system of embodiment 20, wherein the second object is located at a peripheral point of the patient.

23. The system of any of embodiments 16 to 22, further including a third object.

24. The system of any of embodiments 16 to 23, further including, calculating a pulse transit time based on the change in pixel intensity and a movement at the first object and the third object.

25. The system of embodiment 23, further including: comparing the pulse transit time between the first object and the second object with the pulse transit time between the first object and the third object, wherein a difference in the pulse transit time greater than a threshold amount is indicative of an adverse health condition.

26. A method of detecting a heart rate of a patient including: receiving, by a computing device, a first set of images of a patient acquired using an imaging device; receiving, by the computing device, a second set of images of the patient acquired using the imaging device; identifying, by the computing device, a capture point visible in the first set of images and the second set of images, wherein the capture point includes a patch coupled to the patient; computing, by the computing device, a change in the patch between the capture point in the first set of images and the second set of images, wherein the change in the patch is a change in pixel intensity; determining a rate of change of pixel intensity between the first set of images and the second set of images; and computing the heart rate of the patient.

27. The method of embodiment 26, wherein the change in pixel intensity indicates a movement caused by a cardiac cycle.

28. The method of any of embodiments 26 to 27, further including detecting a deformation of the patch.

29. The method of embodiment 28, wherein the deformation is a mechanical deformation.

30. The method of any of embodiments 28 to 29, wherein the deformation is an optical deformation.

31. The method of any of embodiments 28 to 30, wherein the deformation is a thermal deformation.

32. The method of any of embodiments 26 to 31, wherein the patch is retroreflective.

33. The method of any of embodiments 26 to 32, wherein the patch includes at least one optical filter.

34. The method of embodiment 33, wherein the at least one optical filter is a red filter.

35. The method of any of embodiments 33 to 34, wherein the at least one optical filter is a green filter.

36. The method of any of embodiments 33 to 35, wherein the at least one optical filter is an infrared filter.

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components unless the context requires otherwise.

As used herein, the term "based on" can be used synonymously with "based, at least in part, on" and "based at least partly on."

As used herein, the terms "comprises/comprising/comprised" and "includes/including/included," and their equivalents can be used interchangeably. An apparatus, system, or method that "comprises A, B, and C" includes A, B, and C, but also can include other components (e.g., D) as well. That is, the apparatus, system, or method is not limited to components A, B, and C.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles, other written text, and website content throughout this specification (referenced materials herein). Each of the referenced materials is individually incorporated herein by reference in their entirety for their referenced teaching(s), as of the filing date of this application.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the example(s) or when the application of the meaning renders any construction meaningless or essentially meaningless. In cases where the construction of the term would render it meaningless or essentially meaningless, the definition should be taken from Webster's Dictionary, 11th Edition or a dictionary known to those of ordinary skill in the art, such as the Oxford Dictionary of Biochemistry and Molecular Biology, 2$^{nd}$ Edition (Ed. Anthony Smith, Oxford University Press, Oxford, 2006), and/or A Dictionary of Chemistry, 8$^{th}$ Edition (Ed. J. Law & R. Rennie, Oxford University Press, 2020).

Although the subject matter has been described in language specific to structural features and/or methodological acts, it is to be understood that the subject matter defined in the appended claims is not necessarily limited to the specific features or acts described.

What is claimed is:

1. A method for continuous blood pressure monitoring comprising:

receiving, by a computing device, a first set of images of a patient acquired using an imaging device;

receiving, by the computing device, a second set of images of the patient acquired using the imaging device;

identifying, by the computing device, a first capture point and a second capture point on the patient, the first capture point and the second capture point visible in the first set of images and the second set of images, wherein the first capture point comprises a deformable patch coupled to the patient;

computing, by the computing device, a change in the deformable patch and a change in the second capture point between the first set of images and the second set of images, wherein the change is a change in a first pixel intensity and a second pixel intensity;

computing, based on the first change in pixel intensity and the second change in pixel intensity, wherein the first change in pixel intensity is a change in position at the first capture point and the second capture point and the second change in pixel intensity is a change in reflection at the first capture point and the second capture point, a pulse transit time; and computing, based on the pulse transit time, a blood pressure of the patient.

2. The method of claim 1, wherein the second change in the pixel intensity indicates a volumetric change of blood at a skin surface of the patient in response to a heartbeat.

3. The method of claim 1, wherein the patient is illuminated during acquisition of the first or second set of images.

4. The method of claim 1, wherein the patch is retroreflective.

5. The method of claim 1, wherein the deformation is at least one of a mechanical deformation, an optical deformation, or a thermal deformation.

6. The method of claim 1, wherein at least a portion of the patch is retroreflective, and the patch comprises at least one optical filter, wherein the at least one optical filter is a red filter, a green filter, or an infrared filter.

7. The method of claim 1, wherein the change in the second pixel intensity is indicative of a change in light absorption at the first capture point and the second capture point.

8. The method of claim 1, wherein the deformable patch magnifies movement at the first capture point.

* * * * *